US012685859B2

(12) United States Patent
Pouchoulin et al.

(10) Patent No.: US 12,685,859 B2
(45) Date of Patent: Jul. 21, 2026

(54) APPARATUS FOR EXTRACORPOREAL BLOOD TREATMENT, DISPOSABLE ASSEMBLY FOR THE APPARATUS

(71) Applicant: GAMBRO LUNDIA AB, Lund (SE)

(72) Inventors: Dominique Pouchoulin, Tramoyes (FR); Thierry Court, Villeurbanne (FR)

(73) Assignee: Gambro Lundia AB, Lund (SE)

( * ) Notice: Subject to any disclaimer, the term of this patent is extended or adjusted under 35 U.S.C. 154(b) by 691 days.

(21) Appl. No.: 17/919,616

(22) PCT Filed: Mar. 9, 2021

(86) PCT No.: PCT/EP2021/055942
§ 371 (c)(1),
(2) Date: Oct. 18, 2022

(87) PCT Pub. No.: WO2021/213729
PCT Pub. Date: Oct. 28, 2021

(65) Prior Publication Data
US 2023/0149700 A1 May 18, 2023

(30) Foreign Application Priority Data
Apr. 20, 2020    (EP) .................................... 20170402

(51) Int. Cl.
*A61M 60/847*       (2021.01)
*A61M 1/16*         (2006.01)
(Continued)

(52) U.S. Cl.
CPC ........ *A61M 60/847* (2021.01); *A61M 1/1654* (2013.01); *A61M 1/342* (2013.01);
(Continued)

(58) Field of Classification Search
CPC ........ A61M 1/155; A61M 1/14; A61M 1/154; A61M 1/152; A61M 1/342; A61M 1/3424;
(Continued)

(56) References Cited

U.S. PATENT DOCUMENTS 2,954,028 A    9/1960  Smith
4,610,781 A    9/1986  Bilstad
(Continued)

FOREIGN PATENT DOCUMENTS

AU    2014200160    2/2014
EP     2403557      1/2012
(Continued)

OTHER PUBLICATIONS

PCT Search Report and Written Opinion for PCT/EP2021/055942 dated May 26, 2021 (8 pages).
(Continued)

*Primary Examiner* — Philip R Wiest
*Assistant Examiner* — Seth Han
(74) *Attorney, Agent, or Firm* — Mueting Raasch Group

(57) ABSTRACT

There is provided an apparatus for extracorporeal blood treatment, comprising: a treatment unit (10), a blood circuit coupled to the treatment unit (10), a blood pump (22) configured to be coupled to a pump section of the blood circuit, at least two fluid lines (40, 60, 70, 70b, 70c) connected to respective containers (48, 68, 78, 88) and to the blood circuit and/or to the treatment unit (10). The apparatus further comprises a fluid dispatcher (300) having a common zone (310), wherein said at least two fluid lines (40, 60, 70, 70b, 70c) are connected one to the other at said common zone (310) upstream the blood circuit, for selectively allowing fluid flow between said at least two fluid lines (40, 60, 70, 70b, 70c) through said common zone (310).

20 Claims, 10 Drawing Sheets

(51) Int. Cl.

| | | |
|---|---|---|
| *A61M 1/34* | (2006.01) | |
| *A61M 60/113* | (2021.01) | |
| *A61M 60/279* | (2021.01) | |
| *A61M 60/37* | (2021.01) | |
| *A61M 60/851* | (2021.01) | |

(52) U.S. Cl.
CPC ........ *A61M 60/113* (2021.01); *A61M 60/279* (2021.01); *A61M 60/37* (2021.01); *A61M 60/851* (2021.01); *A61M 2205/70* (2013.01)

(58) Field of Classification Search
CPC ...... A61M 1/303; A61M 1/3626; A61M 1/15; A61M 1/34; A61M 1/3401; A61M 2205/12; A61M 1/1565; A61M 1/36224; A61M 1/341; A61M 1/16
See application file for complete search history.

(56) References Cited

U.S. PATENT DOCUMENTS

| | | | | |
|---|---|---|---|---|
| 2003/0138349 | A1* | 7/2003 | Robinson ............ | A61M 1/0218 604/4.01 |
| 2004/0067161 | A1 | 4/2004 | Axelsson | |
| 2007/0278155 | A1 | 12/2007 | Lo | |
| 2009/0124963 | A1* | 5/2009 | Hogard ............. | A61M 1/15632 604/30 |
| 2010/0116740 | A1* | 5/2010 | Fulkerson .......... | A61M 1/1696 210/87 |
| 2010/0168639 | A1* | 7/2010 | Cantu ................ | A61M 1/3441 604/4.01 |
| 2011/0166507 | A1 | 7/2011 | Childers | |
| 2011/0315611 | A1 | 12/2011 | Fulkerson | |
| 2013/0248446 | A1 | 9/2013 | Frugier | |
| 2014/0345386 | A1 | 11/2014 | Wright | |
| 2015/0292529 | A1 | 10/2015 | Thiebaud | |
| 2016/0220748 | A1* | 8/2016 | Pouchoulin ......... | A61M 1/1601 |
| 2017/0043078 | A1* | 2/2017 | Thiebaud ........... | A61M 1/1692 |
| 2018/0110913 | A1 | 4/2018 | Loderer | |
| 2020/0030515 | A1* | 1/2020 | Merchant .......... | A61B 5/02427 |
| 2020/0086034 | A1* | 3/2020 | Turner ............... | A61M 60/279 |

FOREIGN PATENT DOCUMENTS

| | | |
|---|---|---|
| EP | 2612684 | 7/2013 |
| JP | 2006025813 | 2/2006 |
| WO | WO 2004/069311 | 8/2004 |
| WO | WO 2009/073567 | 6/2009 |
| WO | WO 2010/042666 | 4/2010 |
| WO | WO 2010/099816 | 9/2010 |
| WO | WO 2011/002853 | 1/2011 |
| WO | WO 2015/177606 | 11/2015 |

OTHER PUBLICATIONS

Chinese Patent Application No. 2021800298979, filed Mar. 9, 2021; Office Action and Search Report issued Jun. 19, 2025, English language translation included (13 pages).

* cited by examiner

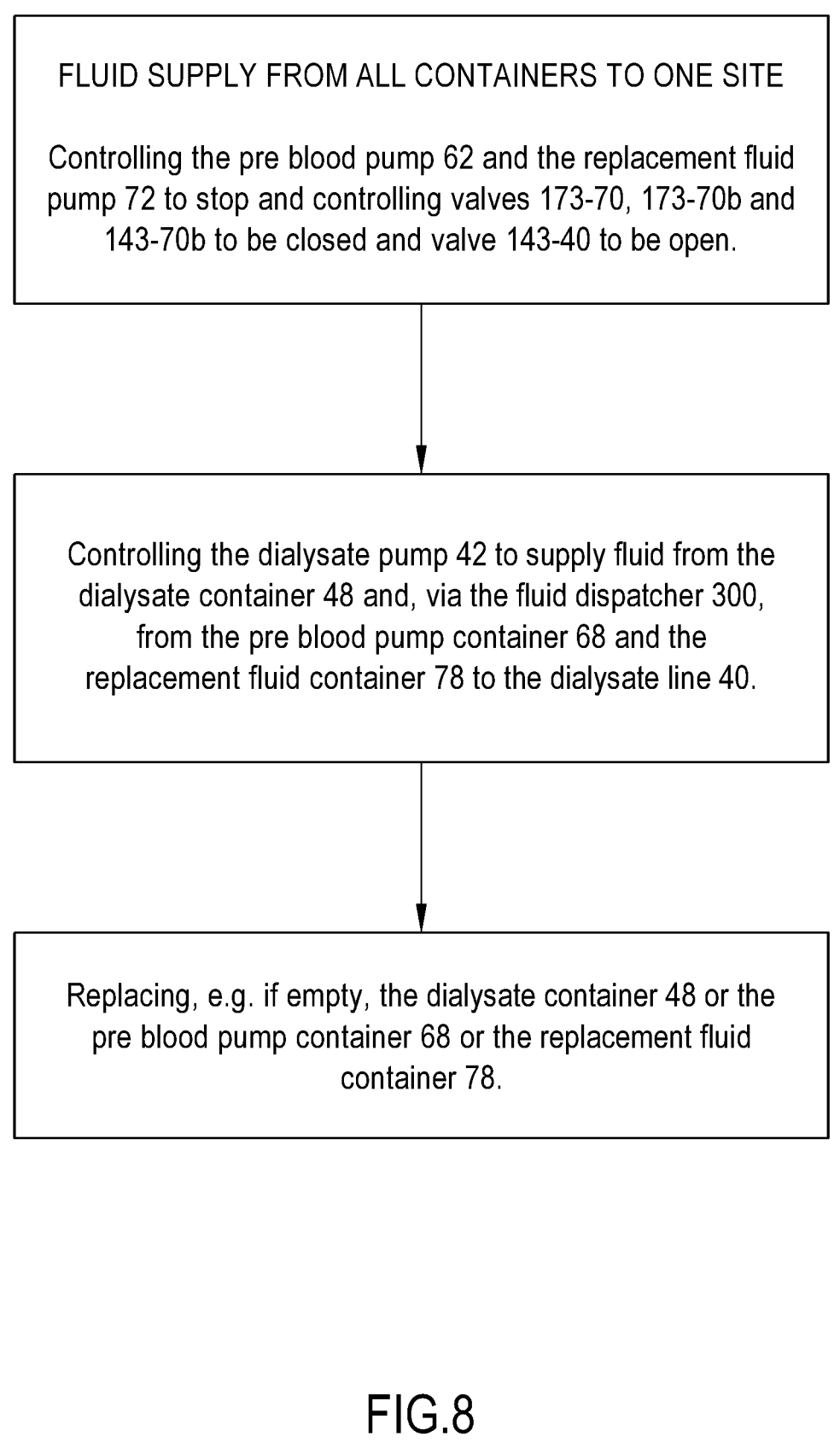

FLUID SUPPLY FROM ALL CONTAINERS TO ONE SITE

Controlling the pre blood pump 62 and the replacement fluid pump 72 to stop and controlling valves 173-70, 173-70b and 143-70b to be closed and valve 143-40 to be open.

Controlling the dialysate pump 42 to supply fluid from the dialysate container 48 and, via the fluid dispatcher 300, from the pre blood pump container 68 and the replacement fluid container 78 to the dialysate line 40.

Replacing, e.g. if empty, the dialysate container 48 or the pre blood pump container 68 or the replacement fluid container 78.

FIG.8

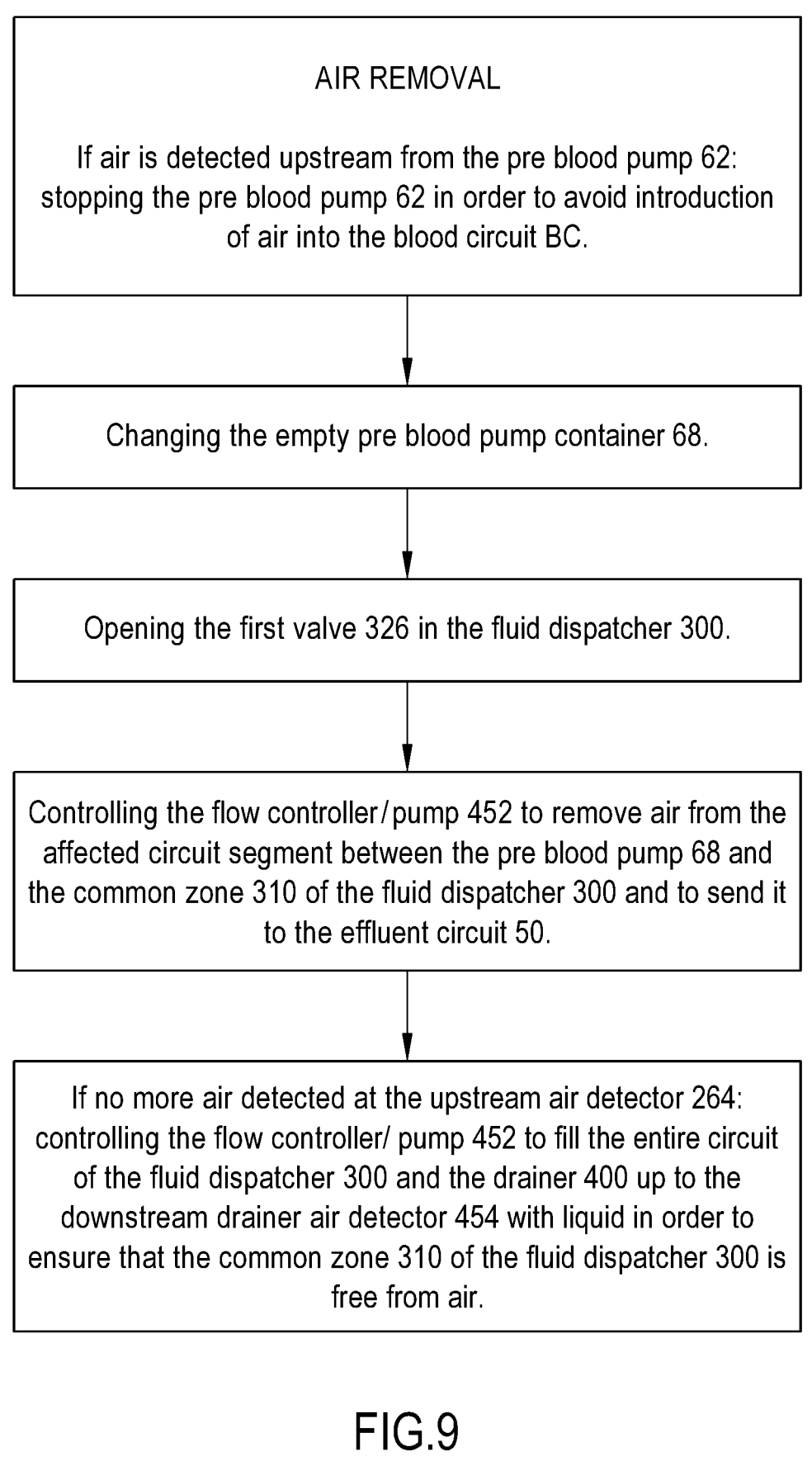

AIR REMOVAL

If air is detected upstream from the pre blood pump 62:
stopping the pre blood pump 62 in order to avoid introduction
of air into the blood circuit BC.

Changing the empty pre blood pump container 68.

Opening the first valve 326 in the fluid dispatcher 300.

Controlling the flow controller/pump 452 to remove air from the
affected circuit segment between the pre blood pump 68 and
the common zone 310 of the fluid dispatcher 300 and to send it
to the effluent circuit 50.

If no more air detected at the upstream air detector 264:
controlling the flow controller/ pump 452 to fill the entire circuit
of the fluid dispatcher 300 and the drainer 400 up to the
downstream drainer air detector 454 with liquid in order to
ensure that the common zone 310 of the fluid dispatcher 300 is
free from air.

FIG.9

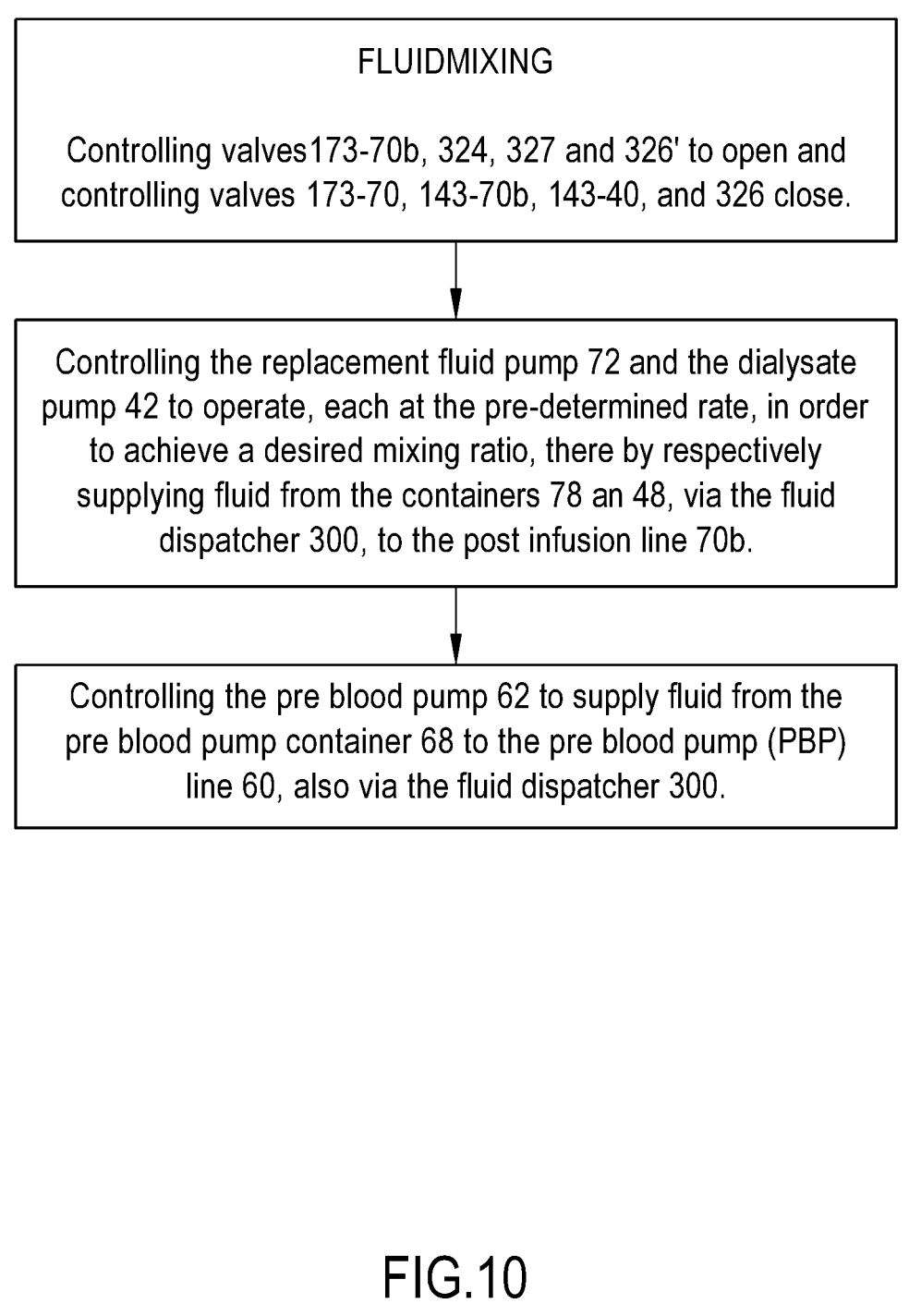

FLUIDMIXING

Controlling valves173-70b, 324, 327 and 326' to open and controlling valves 173-70, 143-70b, 143-40, and 326 close.

Controlling the replacement fluid pump 72 and the dialysate pump 42 to operate, each at the pre-determined rate, in order to achieve a desired mixing ratio, there by respectively supplying fluid from the containers 78 an 48, via the fluid dispatcher 300, to the post infusion line 70b.

Controlling the pre blood pump 62 to supply fluid from the pre blood pump container 68 to the pre blood pump (PBP) line 60, also via the fluid dispatcher 300.

FIG.10

APPARATUS FOR EXTRACORPOREAL BLOOD TREATMENT, DISPOSABLE ASSEMBLY FOR THE APPARATUS

This application is a U.S. National Stage Application of International Application No. PCT/EP2021/055942 filed Mar. 9, 2021, which was published in English on Oct. 28, 2021 as International Publication No. WO 2021/213729 A1. International Application No. PCT/EP2021/055942 claims priority to European Application No. 20170402.0 filed Apr. 20, 2020.

TECHNICAL FIELD

The present invention relates to an apparatus for extracorporeal blood treatment, to a disposable assembly for the apparatus and to a method for controlling an apparatus for extracorporeal blood treatment.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example.

In particular, the invention relates to continuous renal replacement therapy (CRRT) systems. CRRT systems are configured for delivering treatments designed for patients versing in acute states of illness and who have temporarily lost their kidney function in its entirety. In this respect, CRRT systems may be structurally and/or operationally different from extracorporeal blood treatment systems designed for chronic patient care.

CRRT monitors should be able to deliver various therapies (SCUF CCVH, CVVHDF, TPE). The delivery of these therapies requires a specific arrangement of circuit flow-path as well as a number variable of solutions which may be available under bag form.

BACKGROUND OF THE INVENTION

Document U.S. 2015/0292529 discloses a system for treating blood, which includes a single cassette permitting the distribution of the fluids in order to carry out various CRRT treatments. The cassette comprises distribution and connection chambers. One of these distribution chambers comprises an inlet channel and three outlet channels controlled by the controller so as to allow a fluid to be injected into the blood filtration means, into the blood before the blood filtration means and/or after the blood filtration means.

Document U.S. Pat. No. 4,610,781 discloses a fluid processing system including an integral flow control and distribution manifold for establishing fluid communication between conduit segments of the system. The manifold is received in an actuator head of an associated processor apparatus, wherein valving elements selectively crimp valving passageways in the manifold to perform the procedure.

Document WO 2015/177606 discloses a dialysis system comprises a filtration means, a pump, a back filtration system and a sorbent device for performing a dialysis treatment.

Document U.S. 2007/278155 discloses a kidney failure therapy system including a dialysate supply, a valve actuator; a pump actuator and a disposable unit including first and second flexible sheets sealed together for forming a flow path configured to be placed in fluid communication with the dialysate supply and operable with the valve actuator and a pumping portion configured to operate with the at least one pump actuator.

Known issues, problems and limitations associated with known extracorporeal blood treatment systems include, on the fresh fluid circuit side, one or more of the following:

FB1: Reliably detecting air coming from infusion containers and/or reliably avoiding its injection into the blood circuit cannot be easily achieved.

FB2: Injecting fluid coming from several connected fluid containers (simultaneously or alternatively) at a single site (in the blood or dialysate circuit) is typically not provided for.

FB3: Injecting (e.g. once at a time) fluid coming from a single fluid container at different sites is typically not provided for.

FB4: Injecting a customized infusion liquid created by the ratio-metric mixing of fluid coming from two connected containers at a site in the blood circuit is typically not provided for.

FB5: There is typically no provision made for analyzing the composition of fluid coming from a connected fluid container.

Known issues, problems and limitations associated with known extracorporeal blood treatment systems include, on an effluent fluid circuit side:

EB1: Automatic recalibration of effluent sensor/s, e.g. blood leak detectors (BLD), by filling the BLD chamber with fresh dialysate or replacement fluid is typically not provided for.

A general aim of the present invention is to provide for an apparatus for extracorporeal blood treatment that alleviates or minimizes the above-mentioned drawbacks.

It is a further aim of the present invention to provide a method for controlling an apparatus for extracorporeal blood treatment that alleviates or minimizes the above-mentioned drawbacks.

It is in particular aim of the present invention to provide an apparatus for extracorporeal treatment of blood which may be set in a plurality of configurations to deliver various therapies (e.g. SCUF CCVH, CWHDF, TPE) and to accomplish other working requirements, such as:

complete emptying of solution bags;

changing bags without interrupting the fluid exchange therapy;

control of proper mixing of two-compartment bags;

freely choosing infusion site or sites of one or more solution bag/s.

SUMMARY

An apparatus according to one or more of the appended claims, taken singly or in any combination, attain at least one of the above-indicated aims.

An apparatus and a method according to aspects of the invention and capable of achieving one or more of the above objects are here below described.

In a $1^{st}$ independent aspect there is provided an apparatus for extracorporeal blood treatment, comprising: a treatment unit; a blood circuit coupled to the treatment unit and comprising a blood removal line and a blood return line connectable to a vascular system of a patient; a blood pump configured to be coupled to a pump section of the blood circuit;

a plurality of fluid lines connected or connectable to respective containers and to the blood circuit and/or to the treatment unit;

a fluid dispatcher having a common zone, wherein at least two of said plurality of fluid lines are connected one to the other at said common zone upstream the blood circuit, for selectively allowing fluid flow between said at least two fluid lines through said common zone.

Optionally, there is provided an effluent line configured for discharging fluid from the treatment unit.

Optionally, the plurality of fluid lines comprises: a plurality of infusion lines having a second end connected to the blood circuit; wherein at least two infusion lines of said plurality of infusion lines are connected one to the other at said common zone.

Optionally, the plurality of fluid lines comprises: the plurality of infusion lines; a dialysate circuit comprising a dialysate line having a first end connected or connectable to a dialysate container and a second end connected to the treatment unit; wherein the dialysate line and the effluent line are connected one to the other at said common zone.

Optionally, said plurality of fluid lines comprises:

a pre blood pump line having a first end connected or connectable to a pre blood pump container and a second end connected to the blood removal line; and/or a pre-infusion line having a first end connected or connectable to an infusion container and a second end connected to the blood removal line downstream blood pump and/or at least a post infusion line having a first end connected or connectable to an infusion container and a second end connected to the blood return line; and/or a dialysate circuit comprising a dialysate line having a first end connected or connectable to a dialysate container and a second end connected to the treatment unit.

In a $2^{nd}$ aspect according to previous aspect 1, the apparatus comprises an air detector array configured to detect air or gas on each of said at least two fluid lines, optionally in the pre blood pump line, in the pre-infusion line and/or in the post-infusion line and/or in the dialysate line; optionally the air detector array is arranged on the respective line proximate the respective container and/or immediately downstream from the respective pump with respect to a fluid flow from the container.

In a $3^{rd}$ aspect according to aspect 1 or 2, the apparatus comprises a plurality of pumps active on the fluid lines, optionally some pumps of the plurality of pumps are active on the infusion lines, optionally a pre blood pump active on the pre blood pump line and/or an infusion pump active on the pre-infusion line and/or a dialysate pump active on the dialysate line and, optionally and/or an effluent pump active on the effluent line and/or an additional pump active on an additional post-infusion line.

In a $4^{th}$ aspect according to aspect 3 when according to aspect 2, the air detector array is placed upstream or downstream the pumps, optionally upstream or downstream the pre blood pump and/or the infusion pump and/or the dialysate pump and/or the additional pump.

In a $5^{th}$ aspect according to any of aspects 1 to 4, a fluid analyzer is positioned on the effluent line upstream the effluent container or drain and configured for checking/ analyzing composition of fresh or effluent fluids and/or an external fluid analyzer is connected to the effluent line via interface ports.

In a $6^{th}$ aspect according to any of aspects 1 to 5, the apparatus comprises a drainer configured for connecting the fluid lines, optionally the pre blood pump line, the pre-infusion line, the post-infusion line and the dialysate line to the effluent line.

In a $7^{th}$ aspect according to previous aspect 6, the drainer comprises a drainer fluid line, configured for connecting the common zone of the fluid dispatcher to the effluent line, optionally at a junction between an effluent pump and the effluent container or drain.

In a $8^{th}$ aspect according to previous aspect 6 or 7, the drainer comprises a drainer flow controller configured for selectively allowing fluid flow between the common zone and the effluent line.

In a $9^{th}$ aspect, according to previous aspect 8, the drainer flow controller includes: an occlusive pump, optionally a peristaltic pump, wherein a stretch of the drainer fluid line is configured to be coupled to the occlusive pump; or a two-way valve configured to selectively allow or prevent fluid flow.

In a $10^{th}$ aspect according to aspect 7 or to aspects 8 or 9 when according to aspect 7, the drainer comprises a drainer air detector arranged on the drainer fluid line and configured for detecting air or gas in a fluid flow between the common zone of the fluid dispatcher and the effluent line.

In a $11^{th}$ aspect according to aspect 7 or to any of aspects 8 to 10 when according to aspect 7, the drainer fluid line comprises a non-return flow controller configured to allow fluid flow from the common zone of the fluid dispatcher towards the effluent line and to prevent fluid flow from the effluent line towards the common zone, optionally the non-return flow controller comprises a check valve.

In a $12^{th}$ aspect according to aspect 11, the non-return flow controller is arranged on the drainer fluid line downstream from the drainer with respect to fluid flow from the common zone towards the effluent line.

In a $13^{th}$ aspect according to any of aspects 1 to 12, the fluid dispatcher comprises a plurality of valves placed at the common zone and configured for selectively allowing fluid flow between said at least two fluid lines, optionally between the pre blood pump line, the pre-infusion line, the post-infusion line and the dialysate line.

In a $14^{th}$ aspect according to any of aspects 1 to 13, each of said at least two fluid lines includes, upstream or downstream the respective pump with respect to a fluid flow from the respective container, a branch, optionally the fluid dispatcher comprises a pre blood pump line branch departing from the pre blood pump line and/or a pre-infusion line branch departing from the pre-infusion line and/or a dialysate line branch departing from the dialysate line and/or an additional post-infusion line branch departing from the additional post-infusion line, connected one to the other at the common zone.

In a $15^{th}$ aspect according to any of aspects 1 to 14, said at least two fluid lines, optionally the pre blood pump line and/or the pre blood pump line and/or dialysate line and/or the additional post-infusion line, cross/es the common zone.

In a $16^{th}$ aspect according to any of aspects 1 to 15, the fluid dispatcher comprises a valve on each of said at least two fluid lines for selectively allowing fluid flow between the respective line and the common zone; optionally the fluid dispatcher comprises:

a first valve configured for selectively allowing fluid flow between the pre blood pump line and the common zone;

a second valve configured for selectively allowing fluid flow between the pre-infusion line and the common zone; and a third valve configured for selectively allowing fluid flow between the dialysate line and the common zone;

a fourth valve configured for selectively allowing fluid flow between the additional post-infusion line and the common zone.

In a 17$^{th}$ aspect according to previous aspect 16 when according to aspect 14, a branch is connected to a respective valve of the fluid dispatcher; optionally the first valve is placed on the pre blood pump line branch and/or the second valve is placed on the pre-infusion line branch and/or the third valve is placed on the dialysate line branch and/or the fourth valve is placed on the additional post-infusion line branch.

In a 18$^{th}$ aspect according to aspect 16 when according to aspect 3, the pre blood pump line includes, upstream from the pre blood pump with respect to a fluid flow from the pre blood pump container, a pre blood pump line branch connected to the first valve.

In a 19$^{th}$ aspect according to aspect 18 or to aspect 16 when according to aspect 3, the pre-infusion line includes, upstream from the infusion pump with respect to a fluid flow from the pre-infusion container, a pre-infusion line branch connected to the second valve.

In a 20$^{th}$ aspect according to aspect 18 or 19 or to aspect 16 when according to aspect 3, the dialysate line includes, upstream from the dialysate pump with respect to a fluid flow from the dialysate container, a dialysate line branch connected to the third valve.

In a 21$^{st}$ aspect according to aspect 19 or 20 or to aspect 16 when according to aspect 3, the fluid dispatcher includes a flow controller; the pre blood pump line includes, downstream from the pre blood pump with respect to a fluid flow from the pre blood pump container, a pre blood pump line branch connected to the first valve, the flow controller being arranged on the pre blood pump line downstream from the pre blood pump line branch.

In a 22$^{nd}$ aspect according to aspect 18 or 20 or to aspect 16 when according to aspect 3, the fluid dispatcher includes a flow controller; the pre-infusion line includes, downstream from the infusion pump with respect to a fluid flow from the infusion container, a pre-infusion line branch connected to the second valve, the flow controller being arranged on the pre-infusion line downstream from the pre-infusion line branch.

In a 23$^{nd}$ aspect according to aspect 18 or 19 or to aspect 16 when according to aspect 3, the fluid dispatcher includes a flow controller; the dialysate line includes, downstream from the dialysate pump with respect to a fluid flow from the dialysate container, a dialysate line branch connected to the third valve, the flow controller being arranged on the dialysate line downstream from the dialysate line branch.

In a 24$^{th}$ aspect according to previous aspect 23, the flow controller includes a two-way valve configured to selectively allow or prevent fluid flow.

In a 25$^{th}$ aspect according to any of aspects 1 to 24, the fluid dispatcher is configured to allow a bidirectional flow in at least part of said at least two fluid lines, optionally in at least part of the pre blood pump line and/or the pre-infusion line and/or the dialysate line.

In a 26$^{th}$ aspect according to aspect 14 or to any of aspects 17 to 23, the fluid dispatcher is configured to allow a bidirectional flow in the pre blood pump line branch and/or in the pre-infusion line branch and/or in the dialysate line branch.

In a 27$^{th}$ aspect according to aspect 2 or to any of aspects 3 to 26 when according to aspect 2, the air detector array comprises: a pre blood pump air detector arranged on the pre blood pump line.

In a 28$^{th}$ aspect according to previous aspect 27, the pre blood pump air detector is arranged on the pre blood pump line proximate the pre blood pump container and/or immediately downstream from the pre blood pump container with respect to a fluid flow from the pre blood pump container.

In a 29$^{th}$ aspect according to aspect 2 or to any of aspects 3 to 28 when according to aspect 2, the air detector array comprises: a pre-infusion air detector arranged on the pre-infusion line.

In a 30$^{th}$ aspect according to previous aspect 29, the pre-infusion air detector is arranged on the pre-infusion line proximate the pre-infusion container and/or immediately downstream from the pre-infusion container with respect to a fluid flow from the pre-infusion container.

In a 31$^{st}$ aspect according to aspect 2 or to any of aspects 3 to 30 when according to aspect 2, the air detector array comprises: a dialysate air detector arranged on the dialysate line.

In a 32$^{nd}$ aspect according to previous aspect 31, the dialysate air detector is arranged on the dialysate line proximate the dialysate container and/or immediately downstream from the dialysate container with respect to a fluid flow from the dialysate container.

In a 33$^{rd}$ aspect according to any one of the previous aspects 1 to 32, a plurality of flow controllers are placed on the fluid lines and between pumps and infusion sites on the blood removal line and/or blood return line and/or treatment unit; optionally a pre-infusion flow controller is arranged on the pre-infusion line; a dialysate flow controller is arranged on the dialysate line; a post-infusion line has a first end in fluid communication with the pre-infusion flow controller and with the dialysate flow controller and a second end connected to the blood return line; optionally each flow controller includes a two-way valve configured to selectively allow or prevent fluid flow; optionally at least one of the flow controllers is placed on two or more fluid lines and is configured to selectively allow fluid flow into one or more of said two or more fluid lines.

In a 34$^{th}$ aspect according to previous aspect 33, the pre-infusion flow controller is configured to selectively allow fluid flow into the pre-infusion line only, into the post-infusion line only or to both into the pre-infusion line and the post-infusion line.

In a 35$^{th}$ aspect according to previous aspect 33 or 34, the dialysate flow controller is configured to selectively allow fluid flow into the dialysate line only, into the post-infusion line only or into both the dialysate line and the post-infusion line In a 36$^{th}$ aspect according to previous aspects 2 and/or 3 and/or 6 and/or to one or more of the other aspects when according to aspects 2 or 3 or 6, a control unit is connected to the drainer, to the air detector array, to the pumps, optionally to the pre blood pump, the infusion pump, to the dialysate pump and to the fluid dispatcher.

In a 37$^{th}$ aspect according to previous aspect 36, the control unit is configured to control at least one of said pumps, optionally the pre blood pump and/or the infusion pump and/or the dialysate pump, and to control the fluid dispatcher so that fluid/s from one or more, optionally from one, of the pre blood pump container, the infusion container and the dialysate container is/are conveyed to the second end of one or more, optionally to all, of the fluid lines, optionally of the pre blood pump line, the pre-infusion line and the dialysate line.

In a 38$^{th}$ aspect according to previous aspect 36, the control unit is configured to control at least two of the pumps, optionally of the pre blood pump, the infusion pump and the dialysate pump, and to control the fluid dispatcher so that fluids from said at least two, optionally from all, of the pre blood pump container, the pre-infusion container and the dialysate container is mixed and then conveyed to the second end of one or more, optionally of one, of the fluid lines, optionally of the pre blood pump line, the pre-infusion line and the dialysate line.

In a 39$^{th}$ aspect according to previous aspect 36, 37 or 38, the control unit is configured for commanding execution of a task for removing air, said task comprises the following steps:

receiving a signal from the air detector array indicative of detected air presence upstream at least one of the pumps, optionally the pre blood pump or the infusion pump or the dialysate pump;

stopping said at least one of the pumps, optionally the pre blood pump or the infusion pump or the dialysate pumpk, where air presence is detected;

activating the drainer and controlling the fluid dispatcher to remove air after that cause of air presence, optionally due to an empty container, is removed.

In a 40$^{th}$ aspect according to any one of the previous aspects 1 to 39, the effluent line comprises an effluent sensor, optionally a blood leak detector (BLD), optionally positioned close to the effluent container or the drain.

In a 41$^{st}$ aspect according to the previous aspect when according to any of aspects 36 to 39, the control unit is connected to the blood leak detector (BLD) and is configured for commanding execution of a task for calibrating the blood leak detector (BLD), said task comprises the following steps:

controlling the pre blood pump, the infusion pump, the dialysate pump, the effluent pump, the fluid dispatcher and the drainer to supply fluid from the pre blood pump container and/or the infusion container and/or the dialysate container, to the fluid dispatcher and further, via drainer, to the effluent line and to fill the blood leak detector (BLD) with fluid;

performing calibration of the blood leak detector.

In a 42$^{nd}$ aspect according to aspect 5 and/or to one or more of the previous aspects 1 to 42, wherein the interface ports are optionally positioned between the blood leak detector (BLD) and the effluent container or the drain, optionally between the integrated fluid analyzer and the effluent container or the drain.

In a 43$^{rd}$ aspect, there is provided a method for controlling the apparatus for extracorporeal blood treatment according to one or more of the preceding aspects.

In a 44$^{th}$ aspect according to previous aspect 43, the method comprises: conveying fluid/s from one or more containers, optionally from one or more of the pre blood pump container, the infusion container and the dialysate container, to the second end of one or more, optionally to all, the fluid lines, optionally to the second end of one or more of the pre blood pump line, the pre-infusion line and the dialysate line by controlling the pumps, optionally by controlling the pre blood pump and/or the infusion pump and/or the dialysate pump and the fluid dispatcher.

In a 45$^{th}$ aspect according to previous aspect 43, the method comprises: mixing fluids from at least two, optionally from all, of the containers, optionally of pre blood pump container, the pre-infusion container and the dialysate container and then conveying mixed fluids to the second end of one or more, optionally of one, of the fluid lines, optionally of the pre blood pump line, the pre-infusion line and the dialysate line by controlling the pumps, optionally the pre blood pump and/or the infusion pump and/or the dialysate pump and the fluid dispatcher.

In a 46$^{th}$ aspect according to previous aspect 43, the method comprises:

receiving a signal from the air detector array indicative of detected air presence upstream at least one of the pumps, optionally the pre blood pump or the infusion pump or the dialysate pump;

stopping said at least one of the pumps, optionally the pre blood pump or the infusion pump or the dialysate pumpk, where air presence is detected;

activating the drainer and controlling the fluid dispatcher to remove air after that cause of air presence, optionally due to an empty container, is removed.

In a 47$^{th}$ aspect according to previous aspect 43, the method comprises: controlling the pumps, optionally pre blood pump, the infusion pump, the dialysate pump, the effluent pump, the fluid dispatcher and the drainer to supply fluid from the containers, optionally the pre blood pump container and/or the infusion container and/or the dialysate container to the fluid dispatcher and further, via drainer, to the effluent line.

In a 48$^{th}$ aspect according to previous aspect 47, the method comprises: filling the blood leak detector (BLD) with fluid of the effluent line and performing calibration of the blood leak detector; and/or checking/analyzing composition of fresh or effluent fluids of the effluent line through the fluid analyzer.

In an independent 49$^{th}$ aspect there is provided a disposable assembly for an apparatus for extracorporeal blood treatment, wherein the disposable assembly comprises: a treatment unit; a blood circuit coupled to the treatment unit and comprising a blood removal line and a blood return line connectable to a vascular system of a patient; wherein the blood circuit has a pump section configured to be coupled to a blood pump of the apparatus for extracorporeal blood treatment;

a plurality of fluid lines connected or connectable to respective containers and to the blood circuit and/or to the treatment unit;

wherein at least two of said plurality of fluid lines are connected one to the other at a common zone and upstream the blood circuit, for selectively allowing fluid flow between said at least two fluid lines through said common zone.

In a 50$^{th}$ aspect according to previous aspect 49, the treatment unit, the blood circuit and the plurality of fluid lines of the apparatus of the previous aspects 1 to 42 are part of the disposable assembly of previous aspect 49 and/or of one of the following aspects 51 to 69.

In a 51$^{st}$ aspect according to any one of the previous aspects 49 and 50, the disposable assembly comprises an effluent line configured for discharging fluid from the treatment unit.

In a 52$^{nd}$ aspect according to any one of the previous aspects 49 to 51, said plurality of fluid lines comprises: a pre blood pump line having a first end connected or connectable to a pre blood pump container and a second end connected to the blood removal line; and/or a pre-infusion line having a first end connected or connectable to an infusion container and a second end connected to the blood removal line downstream blood pump; and/or at least a post-infusion line having a first end connected or connectable to an infusion container and a second end connected to the blood return line; and/or a dialysate circuit comprising a dialysate line having a first end connected or connectable to a dialysate container and a second end connected to the treatment unit.

In a $53^{rd}$ aspect according to any one of the previous aspects 49 to 52, each of said plurality of fluid lines has a pump section configured to be coupled to a respective fluid pump.

In a $54^{th}$ aspect according to any one of the previous aspects 49 to 53, each of said plurality of fluid lines has an air detector section configured to be coupled to an air detector array.

In a $55^{th}$ aspect according to any one of the previous aspects 49 to 54, the disposable assembly comprises a drainer fluid line configured to be coupled to a drainer configured for connecting the fluid lines to the effluent line.

In a $56^{th}$ aspect according to previous aspect 55, the drainer fluid line is configured for connecting the common zone to the effluent line.

In a $57^{th}$ aspect according to previous aspect 55 or 56, the drainer fluid line comprises a flow controller section configured to be coupled to a drainer flow controller configured for selectively allowing fluid flow between the common zone and the effluent line.

In a $58^{th}$ aspect according to any one of the previous aspects 55 to 57, the drainer fluid line comprises an air detector section configured to be coupled to a drainer air detector configured for detecting air or gas in a fluid flow between the common zone of the fluid dispatcher and the effluent line.

In a $59^{th}$ aspect according to any one of the previous aspects 55 to 58, the drainer fluid line comprises a non-return flow controller configured to allow fluid flow from the common zone towards the effluent line and to prevent fluid flow from the effluent line towards the common zone.

In a $60^{th}$ aspect according to any one of the previous aspects 49 to 59, each of said at least two fluid lines includes a branch departing upstream or downstream the respective pump section with respect to a fluid flow from the respective container; wherein the branches are connected one to the other at the common zone.

In a further depending aspect $60^{th}$ bis according to any one of the previous aspects 49 to 60, wherein at least the pre blood pump line is connected to the pre-infusion line and/or to the post-infusion line and/or to the dialysate line at the common zone and upstream the blood circuit, for selectively allowing fluid flow between said fluid lines through said common zone.

In a further depending aspect $60^{th}$ ter according to the previous aspects 49 to 60 bis, wherein the pre blood pump line includes a branch departing upstream or downstream the pump section with respect to a fluid flow from the container; wherein the branch is connected to the common zone.

In a $61^{st}$ aspect according to previous aspect 60 or 60 ter, each branch is connected or connectable to a respective valve of the fluid dispatcher.

In a $62^{nd}$ aspect according to any one of the aspects 60 to 61 when according to aspect 52, the pre blood pump line includes, upstream or downstream the pre blood pump section with respect to a fluid flow from the pre blood pump container, a pre blood pump line branch connected or connectable to a first valve.

In a $63^{rd}$ aspect according to any one of the aspects 60 to 62 when according to aspect 52, the pre-infusion line and/or the post-infusion line includes, upstream or downstream the infusion pump section with respect to a fluid flow from the pre-infusion container, a pre-infusion line branch connected or connectable to a second valve.

In a $64^{th}$ aspect according to any one of the aspects 60 to 64 when according to aspect 52, the dialysate line includes, upstream or downstream the dialysate pump section with respect to a fluid flow from the dialysate container, a dialysate line branch connected or connectable to a third valve.

In a $65^{th}$ aspect according to any one of the previous aspects 49 to 64, each of said plurality of fluid lines has a flow controller section configured to be coupled to a flow controller placed between pumps and infusion sites.

In a $66^{th}$ aspect according to aspect 51, the effluent line comprises an effluent sensor or is configured to be coupled to an effluent sensor, optionally a blood leak detector (BLD), optionally positioned close to the effluent container or the drain.

In a $67^{th}$ aspect according to previous aspect 66, the effluent line comprises interface ports configured to connect a fluid analyzer, wherein the interface ports are optionally positioned between the blood leak detector (BLD) and the effluent container or the drain.

In a $68^{th}$ aspect according to any one of the previous aspects 49 to 66, the blood circuit and/or the plurality of fluid lines comprise tubes, optionally flexible tubes, optionally made of plastic.

In a $69^{th}$ aspect according to the previous aspect 68, the tubes of said at least two of said plurality of fluid lines are connected one to the other through bonding, welding or joints, optionally Y or T joints.

In a $70^{th}$ aspect according to any one of the previous aspects, wherein said fluid lines includes a pre infusion line for infusing fluid into the blood circuit upstream the treatment unit, the pre infusion line comprising a post infusion branch for infusing fluid into the blood circuit downstream the treatment unit, optionally said post infusion branch being placed downstream the pump tube tract of said pre infusion line.

In a $71^{st}$ aspect according to any one of the previous aspects, wherein said fluid lines includes a dialysate line for directing fluid to the second chamber of the treatment unit, the dialysate line including a dialysate post infusion branch for infusing fluid into the blood circuit downstream the treatment unit, optionally said dialysate post infusion branch being placed downstream the pump tube tract of said dialysate line.

In a $72^{nd}$ aspect according to the previous aspects 70 and 71, the post infusion branch and the dialysate post infusion branch share a common end length for directly infusing into the blood circuit downstream the treatment unit, particularly, the common end length infusing directly into a bubble trap placed on the blood return line.

In a $73^{rd}$ aspect, the apparatus for extracorporeal blood treatment of the aspects 1 to 42 comprises a machine and the disposable assembly according to any one of the previous aspects 49 to 72; wherein the machine comprises a main body comprising at least the blood pump, the fluid pumps and the control unit; wherein the main body is configured to hold the disposable assembly during treatment.

In a $74^{th}$ aspect, the machine comprises the fluid dispatcher and/or the air detector array and/or the fluid drainer and/or the flow controllers and/or the fluid analyzer.

Further characteristics of the present invention will better emerge from the detailed description that follows of some embodiments of the invention, illustrated by way of non-limiting examples in the accompanying Figures of drawings.

DESCRIPTION OF THE DRAWINGS

The description will now follow, with reference to the appended Figures, provided by way of non-limiting example, in which:

FIGS. 8 to 10 show flowcharts of embodiments of a method for controlling an extracorporeal blood treatment apparatus in accordance with the present invention.

DETAILED DESCRIPTION

Figures 1, 2:
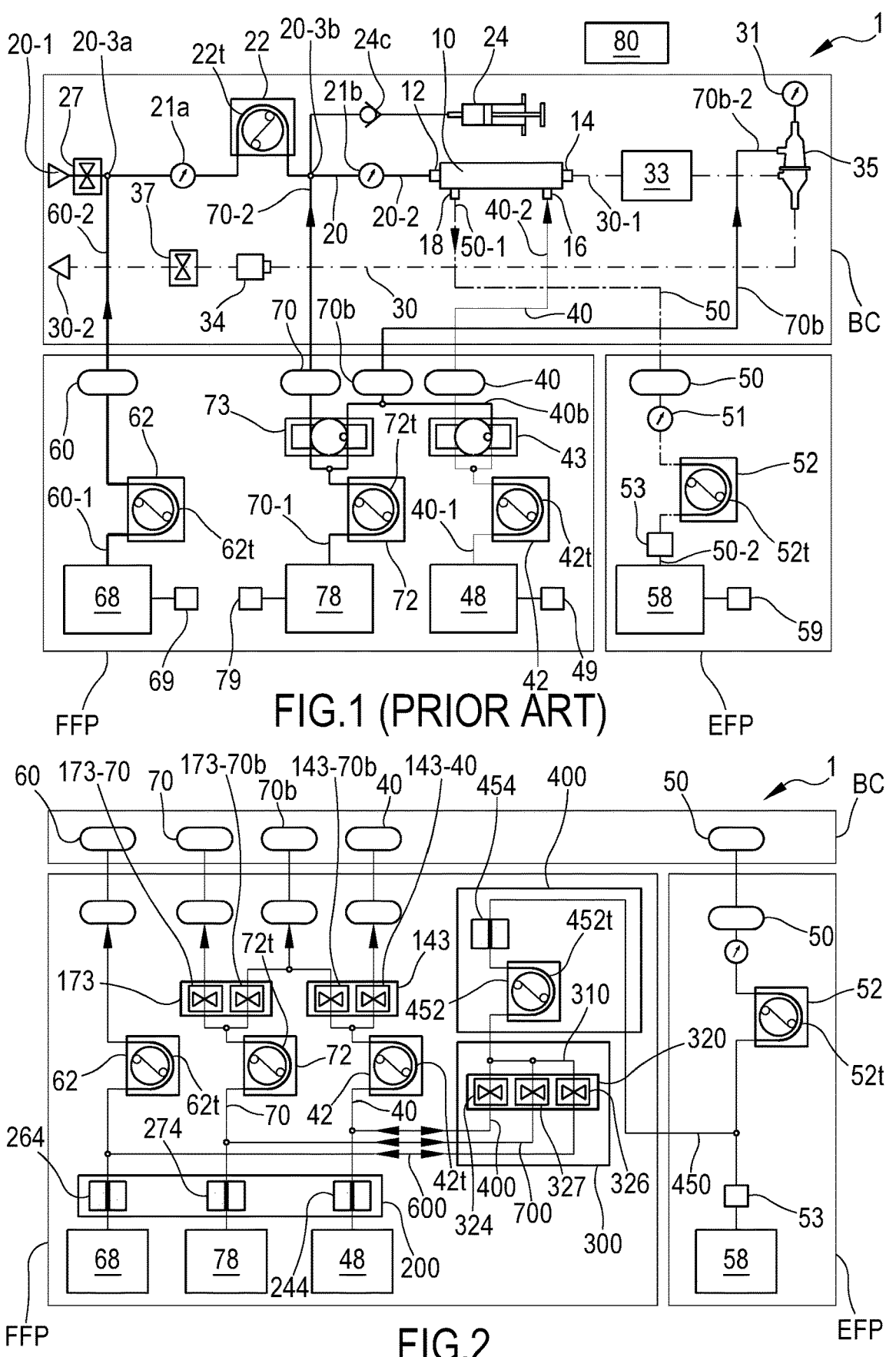
FIG. 1 schematically shows an extracorporeal blood treatment apparatus in accordance with a prior art example.
FIGS. 2, 2A, and 2B schematically show an extracorporeal blood treatment apparatus in accordance with a first embodiment of the present invention.

FIG. 1 schematically shows an extracorporeal blood treatment apparatus in accordance with an example of prior art. The extracorporeal blood treatment apparatus 1 comprises an extracorporeal blood circuit BC coupled to a treatment unit 10, a fresh fluid flow path FFP and an effluent fluid flow path EFP. The fresh fluid flow path FFP and the effluent fluid flow path EFP shown in FIG. 1 are part of an hydraulic circuit of the prior art.

The treatment unit 10, for example a dialyzer, a plasma-filter, a hemofilter, or a hemodiafilter, includes a first chamber and a second chamber, which are separated by a semipermeable membrane, for example of the hollow-fiber type or of the plate type.

The apparatus 1 comprises the blood circuit BC (including the treatment unit 10, a blood removal line 20, a blood return line 30 and, optionally, a blood warmer 33 and/or an air separator/bubble trap 35 provided with a pressure sensor 31) and a dialysate circuit comprising the treatment unit 10, a dialysate line 40 and an effluent line 50.

It is noted that the first chamber of treatment unit 10 is understood to be part of the blood circuit BC, being connected to the blood removal line 20 and to the blood return line 30, and that the second chamber of treatment unit 10 is understood to be part of the dialysate circuit, being connected to the dialysate line 40 and the effluent line 50. Thus, treatment unit 10 may be considered a component of both the blood circuit BC and of the dialysate circuit. In some embodiments, the apparatus 1 comprises additional fluid lines, like a pre blood pump (PBP) line 60, a pre-infusion line 70 and a post-infusion line 70b.

The dialysate line 40, the pre blood pump (PBP) line 60, the pre-infusion line 70 and the post-infusion line 70b are part of the fresh fluid flow path FFP. The effluent line 50 is part of the effluent fluid flow path EFP. In the example shown in FIG. 1, the fresh fluid flow path FFP and the effluent fluid flow path EFP are shown as schematically separated elements merely for clarity. It is noted that the distinction between FFP and EFP as shown in FIG. 1 (and in some subsequent Figures) does not entail any structural, operational, or otherwise shape or form corresponding to the separated elements shown in any of the Figures.

The blood removal line 20 has a first end 20-1 designed to connect to the vascular system of a patient. The particular manner of fluidly connecting the first end 20-1 of the blood removal line 20 to the vascular system of a patient may be realized in accordance with known components and methods. The blood removal line 20 further includes a second end 20-2 configured to connect to the treatment unit 10, in particular to an inlet port 12 of a first chamber of the treatment unit 10. A blood pump 22 is coupled to a section of the blood removal line 20.

The blood return line 30 has a first end 30-1 configured to connect to the treatment unit 10, in particular to an outlet port 14 of the first chamber of the treatment unit 10. The blood return line 30 further has a second end 30-2 designed to connect to the vascular system of the patient. The particular manner of fluidly connecting the second end 30-2 of the blood return line 30 to the vascular system of a patient may be realized in accordance with known components and methods.

The dialysate line 40 is configured for supplying dialysate to the treatment unit 10 and the effluent line 50 is configured for discharging used fluid from the treatment unit 10 towards a drain (not shown) or into a corresponding effluent fluid container 58. The dialysate line 40 has a first end 40-1 configured to connect to a dialysate container 48, such as a dialysate bag or other source of dialysate fluid, and a second end 40-2 configured to connect to an inlet port 16 of the second chamber of the treatment unit 10. A dialysate pump 42 is coupled to a section of the dialysate line 40.

The effluent line 50 has a first end 50-1 configured to connect to an outlet port 18 of the second chamber of the treatment unit 10 and a second end 50-2 configured to connect to the effluent fluid container 58 configured to receive used fluid from the second chamber of the treatment unit 10. In some embodiments, the second end 50-2 of the effluent line is directly connected to the drain and configured to discharge used fluid directly to the drain. An effluent pump 52 is coupled to a section of the effluent line 50. A blood leak detector (BLD) 53 is installed on the effluent line 50 between the effluent pump 52 and the effluent fluid container 58.

The pre blood pump (PBP) line 60 has a first end 60-1 connected to a pre blood pump container 68 and a second end 60-2 configured to connect to the blood removal line 20. A pre blood pump 62 is coupled to a section of the pre blood pump (PBP) line 60.

The pre-infusion line 70 has a first end 70-1 configured to connect to a replacement fluid container 78 and a second end 70-2 configured to connect to the blood removal line 20. A replacement fluid pump 72 is coupled to a section of the pre-infusion line 70.

The post-infusion line 70b branches off from the pre-infusion line 70 at a branch 73 placed downstream the replacement fluid pump 72. The post-infusion line 70b has a second end 70b-2 configured to connect to the blood return line 30. The branch typically includes a flow controller (e.g. one or more valves or a clamp mechanism) configured to selectively enable fluid flow either through the pre-infusion line 70 or through the post infusion line 70b.

Each of the dialysate container 48, the effluent fluid container 58, the pre blood pump container 68 and the replacement fluid container 78 is monitored by a respective sensor 49, 59, 69, 79 configured to detect an amount of fluid in the container.

The replacement fluid pump 72, active on the pre-infusion line 70 and arranged upstream branch 73 (with respect to fluid flow from the replacement fluid container 78 towards branch 73), is configured to supply replacement fluid from the replacement fluid container 78 to the blood circuit 20, 30. Branch 73 (including, e.g., a flow controller, valve(s), and/or clamp(s); see above) is configured to selectively allow supply of replacement fluid from the replacement fluid container 78 through the pre-infusion line 70 or through the post-infusion line 70b. In case of pre-infusion, the replacement fluid is introduced into the blood removal line 20 at a first pre-infusion site 20-3b upstream the treatment unit 10 (with respect to fluid flow from the first end 20-1 of the blood removal line 20 to the second end 20-2 of the blood removal line 20). In case of post-infusion, the replacement fluid is introduced into the blood return line 30 downstream from the treatment unit 10 (with respect to fluid flow from the first end 30-1 of the blood return line 30 to the second end 30-2 of the blood return line 30). An anticoagulant syringe 24 provided with a check valve 24c may be connected to the blood removal line 20 at the first pre-infusion site 20-3b.

The hydraulic circuit may further comprise a second dialysate line 40b, which branches off from the dialysate line 40 at a branch 43. The branch typically includes a flow controller (e.g. one or more valves or a clamp mechanism) configured to selectively enable fluid flow either (solely) through the dialysate line 40 (i.e. from the first end 40-1 thereof to the second end 40-2 thereof) or, alternatively, through the first part of the dialysate line 40 up to branch 43 and further through second dialysate line 40b and post infusion line 70b (i.e. from the first end 40-1 of dialysate line 40 to branch 43, through second dialysate line 40b and post infusion line 70b, to the second end 70b-2 of post infusion line 70b). In detail, dialysate pump 42, active on the dialysate line 40 and arranged upstream the branch 43 (with respect to fluid flow from the dialysate container 48 towards branch 43), is configured to supply dialysate from the dialysate container 48 to treatment unit 10. Branch 43 (including, e.g., a flow controller, valve(s), and/or clamp(s); see above) is configured to selectively allow supply of dialysate from dialysate container 48 through the dialysate line 40 or through the second dialysate line 40b, and, subsequently further through post infusion line 70b.

Within the scope of this description, the terms "upstream" and "downstream" are based on a general direction of fluid flow along a fluid line and/or through components of the apparatus under treatment condition (e.g. from a first end of a line towards a second end of a line; and/or from an arterial access of a patient towards a venous access of a patient). In general (e.g. during treatment), fluid flows through the blood removal line 20, treatment unit 10, and blood return line 30 from the first end 20-1 of the blood removal line 20 towards the second end 30-2 of the blood return line 30. Further, fluid flows from containers 48, 68, and 78 towards the blood circuit, while used fluid flows from the treatment unit 10 towards and into container 58 (or, alternatively, towards and into the drain). Unless otherwise specified, the terms upstream and downstream refer to the above general directions of fluid flow through lines and components during regular operation of the apparatus (e.g. during treatment).

The extracorporeal blood treatment apparatus 1 further comprises a control unit 80, i.e. a programmed/programmable control unit, configured to control components of the apparatus (e.g. pumps, valves, clamps) and to receive signals from components (e.g. sensors). The control unit 80 may, for example, comprise one or more digital microprocessor units or one or more analog units or other combinations of analog units and digital units. The extracorporeal blood treatment apparatus 1 may further comprise a user interface (e.g. a graphic user interface or GUI). The user interface is also connected to control unit 80 and configured to both present information to a user or operator through an output unit (e.g. screen, touchscreen, monitor, led elements, etc.) and to receive input from the user/operator through an input unit (e.g. keyboard, hardware button(s), mouse, touchscreen, voice recognition, optical recognition).

As shown in FIG. 1, the apparatus 1 may include a clamp 37 configured to receive a portion of the blood return line 30 and configured to clamp (e.g. close) fluid flow through the blood return line 30, in particular proximal to the second end 30-2 of the blood return line 30. Similarly, the apparatus 1 may further include a clamp 27 configured to receive a portion of the blood removal line 20 and configured to clamp (e.g. close) fluid flow through the blood removal line 20, in particular proximal to the first end 20-1 of the blood removal line 20.

Each one of the pumps 22, 42, 52, 62, 72 included in the extracorporeal blood treatment apparatus 1 may comprise a positive displacement pump, such as a peristaltic pump. Peristaltic pumps generally operate on a respective pump tube tract (e.g. 22t, 42t, 52t, 62t, 72t) configured to operably connect with the respective pump (22, 42, 52, 62, 72) such that pump motion (e.g. rotation) is transferred onto the pump tube tract, thereby moving a respective fluid along the respective pump tube tract and, thus, through the respective line or lines (20, 40, 40b, 50, 60, 70, 70b) as well as other components (e.g. treatment unit 10, blood warmer 33, and/or air separator/bubble trap 35).

Figure 2A:
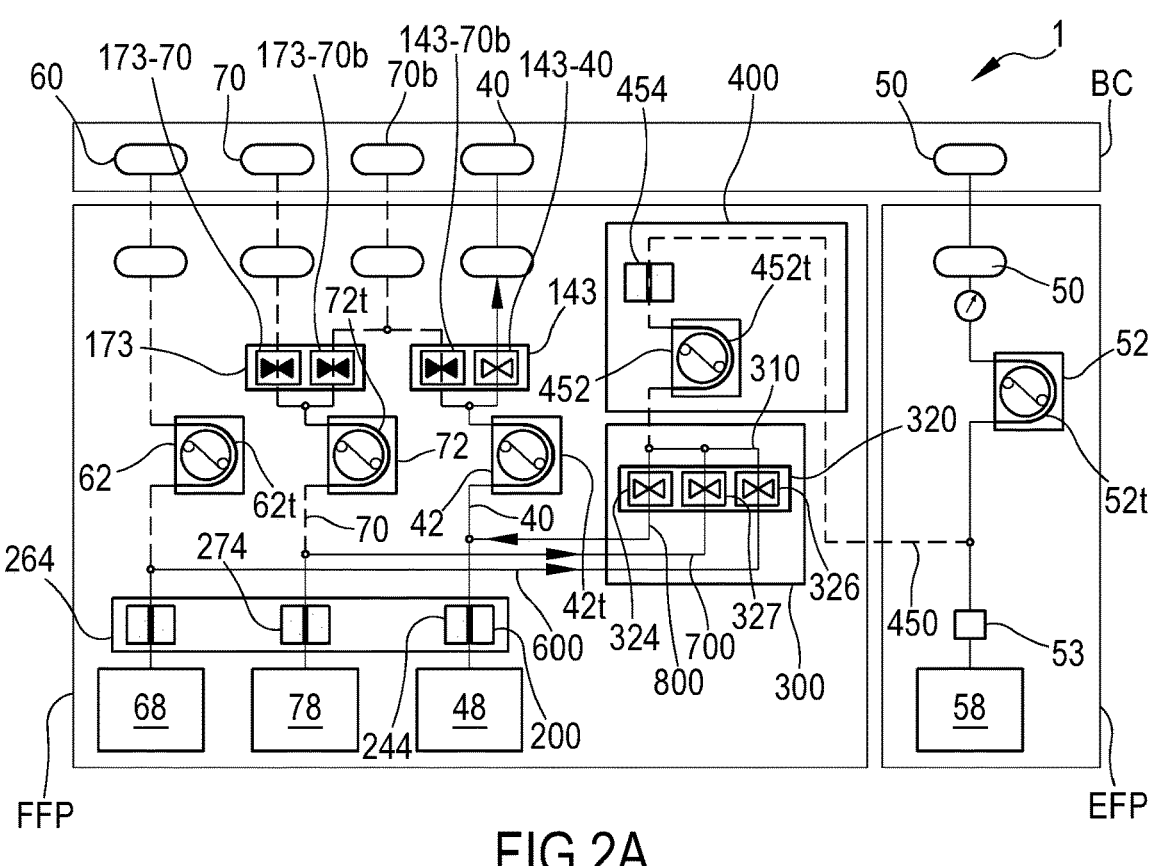
Figure 2B:
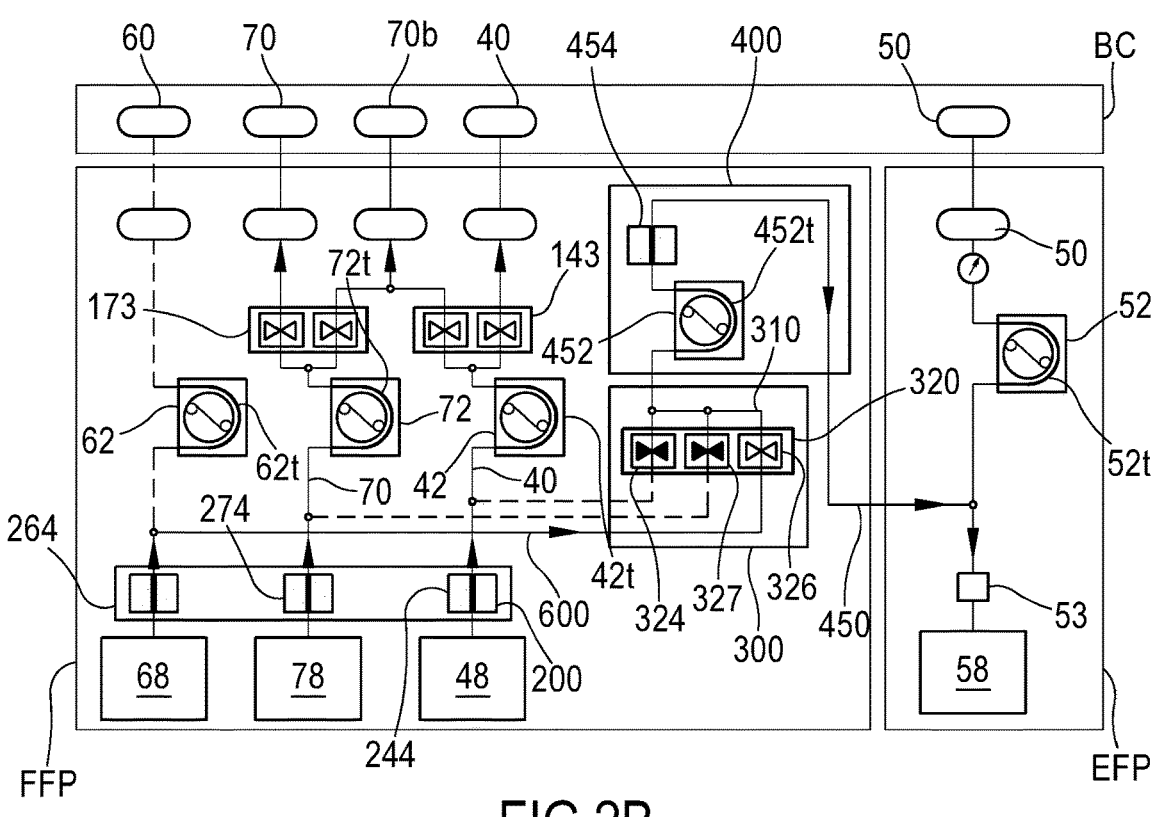

FIGS. 2, 2A, and 2B schematically show an extracorporeal blood treatment apparatus in accordance with a first embodiment of the present invention.

The blood circuit BC is only represented schematically because may be the same as disclosed in the example of prior art of FIG. 1.

According to the first embodiment, the hydraulic circuit (fresh fluid flow path FFP and effluent flow path EFP) according to the invention is provided with an air detector array 200 of air detectors 264, 274, 244 positioned (optionally immediately) downstream from the fluid containers 68, 78, 48 and upstream of the respective pumps 62, 72, and 42. The air detectors 264, 274, 244 are connected to the control unit 80 and are configured to detect any gas or air in the fluid flowing through. The air detectors 264, 274, 244 are each configured to send a respective signal to the control unit 80, the signal being indicative of gas or air detected in the fluid flowing through the respective air detector 264, 274, 244.

According to the first embodiment, the hydraulic circuit (fresh fluid flow path FFP and effluent flow path EFP) is provided with a fluid dispatcher 300 including a plurality of valves 320 configured to control fluid flow between a respective fluid line 60, 70, 40 and a common zone 310 of the fresh fluid dispatcher. The control unit 80 is connected to the fluid dispatcher 300, optionally to each valve 326, 327, 324 of the plurality of valves 320, and configured to control the fluid dispatcher 300, optionally to control (e.g. control to open or close) each valve 326, 327, 324 of the plurality of valves 320.

In this manner, above-described problem FB2 may be addressed in that any one of lines 60, 70, 40 may be put in fluid communication with any one of pumps 62, 72, 42 so that the fluid from any one of containers 68, 78, 48 may be supplied to the blood circuit BC by any one of pumps 62, 72, 42 (each to a different site, see above). In other words, any one of pumps 62, 72, 42 may pump fluid from one or more of containers 68, 78, 48.

The plurality of valves 320 includes a first valve 326 configured to selectively put the pre blood pump (PBP) line 60 in fluid communication with the common zone 310. The plurality of valves 320 further includes a second valve 327 configured to selectively put the infusion line 70 in fluid communication with the common zone 310. The plurality of valves 320 further includes a third valve 324 configured to selectively put the dialysate line 40 in fluid communication with the common zone 310. Each of the connection to lines 60, 70, 40 branches off the respective line optionally downstream the fluid containers 68, 78, 48 (and downstream from the array 200) and upstream from the pumps 62, 72, 42 such that the fresh fluid dispatcher 300 is configured to receive fresh fluid from containers 68, 78, and/or 48, which has been checked for air or gas and configured to supply received fluid to pumps 62, 72, and/or 42.

The hydraulic circuit further includes an air and fluid drainer 400 comprising a flow controller 452 (e.g. a pump, optionally an occlusive pump) and a drainer air detector 454. The air and fluid drainer 400 is in fluid connection with the common zone 310 of the fluid dispatcher 300 and with the effluent line 50 of the effluent fluid flow path. A connecting drainer fluid line 450 branches off the effluent line 50 downstream effluent pump 52 and upstream the drain or the effluent fluid container 58.

This arrangement of an air and fluid drainer 400 allows for sending any mix of air and fluid previously detected upstream from pumps 62, 72, 42 by (any one or more of) the air detectors 264, 274, and/or 244, in order to address the above-described problem FB1.

Further, this arrangement allows for sending fresh fluid from (any one or more of) containers 68, 78, 48 to the effluent line 50 and, in particular, to blood leak detector (BLD) 53 in the effluent line 50. In this manner, the blood leak detector 53 may be (re-) calibrated when the effluent pump 52 is stopped such that only fresh fluid is sent through the effluent line 50 from the air and fluid drainer 400. This addresses the above-described problem EB1.

In one example, for (re-) calibrating the blood leak detector 53, any one or more of valves 326, 327, and/or 324 may be opened while pumps 62, 72, 42, and 52 remain stopped. Upon operation of flow controller/pump 452, fresh fluid is drawn from the one or more containers 68, 78, 48 and conducted through the drainer fluid line 450 and into the effluent line 50 towards the drain or container 58. The fresh fluid also passes through the blood leak detector 53 so that the (re-) calibration may be performed. It is noted that, to this aim, the control unit 80 is connected to the respective components (e.g. sensors, pumps, valves) and configured to operate such components according to the above.

Figure 7:
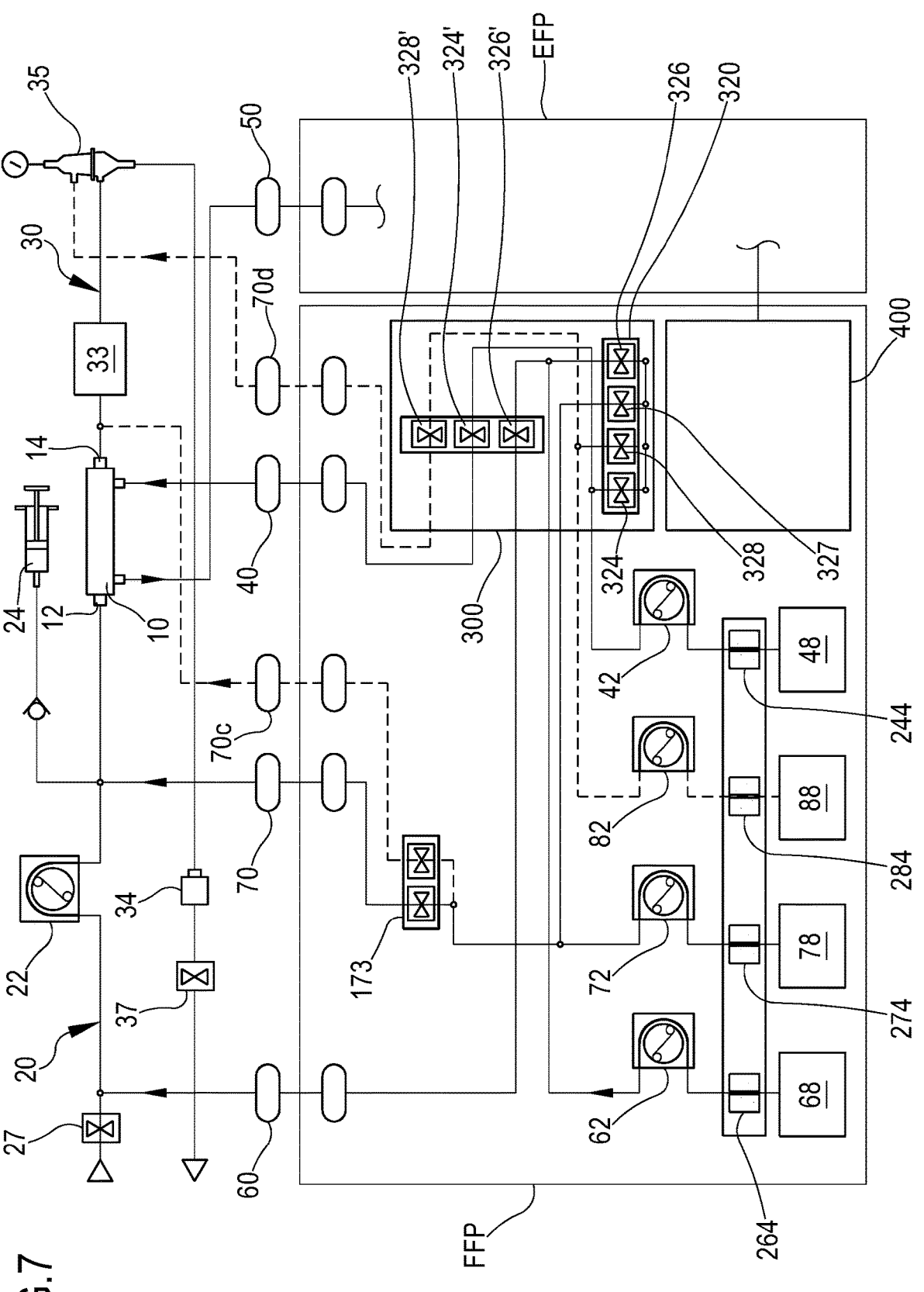
FIG. 7 schematically show an extracorporeal blood treatment apparatus in accordance with a third embodiment of the present invention.

FIGS. 2A and 7 schematically show an example configuration of the extracorporeal blood treatment apparatus in accordance with the first embodiment of the present invention. As described above, the fresh fluid dispatcher 300 may be configured to alternatively associate one or more connected containers 68, 78, 48 to a single fluid pump. In this example, pre blood pump 62 and replacement fluid pump 72 are controlled to stop, while dialysate pump 42 is controlled to supply fluid from the dialysate container 48 and, via the fluid dispatcher 300, from the pre blood pump container 68 and the replacement fluid container 78 to the dialysate line 40. As shown, valves 173-70, 173-70b and 143-70b are controlled to be closed and valve 143-40 is controlled to be open. The example of FIG. 2A shows a configuration in which fluid from all containers 68, 78, 48 is supplied to the dialysate pump 42. This addresses the above-described problem FB2 and further allows replacement of an empty container without stopping blood circulation and/or therapy. Any container 68, 78, 48 may be replaced, e.g. if empty, during an ongoing treatment since fluid from the remaining container or containers may be supplied as shown. Although fluid is supplied from several containers, fluid flow is always controlled by the respective pump (in the example shown, by the dialysate pump 42).

FIGS. 2B and 8 schematically show another example configuration of the extracorporeal blood treatment apparatus in accordance with the first embodiment of the present invention. When air is detected (see problem FB1 above) upstream from a fluid pump (in the example shown, upstream the pre blood pump 62), the pre blood pump 62 is stopped in order to avoid introduction of air into the blood circuit BC. If the associated fluid container, here the pre blood pump container 68, is empty, an operator may change the container. After that, the relevant valve (first valve 326) may be opened in fluid dispatcher 300. Subsequently, the flow controller/pump 452 is controlled to remove air from the affected circuit segment (in the example shown between the pre blood pump 68 and the common zone 310 of the fluid dispatcher 300) and to send it to the effluent circuit 50. The flow controller/pump 452 may be controlled to operate while air is detected by the respective upstream air detector (here air detector 264). When there is no more air detected at the upstream air detector 264, the flow controller/pump 452 is further controlled to operate in order to fill the entire circuit of the fluid dispatcher 300 and the drainer 400 up to the downstream drainer air detector 454 with liquid in order to ensure that the common zone 310 of the fluid dispatcher 300 is free from air. It is noted that, during this procedure, it may be necessary to deactivate/disable blood leak detector 53 in order to prevent a false alarm (e.g. due to the detection of air by blood leak detector 53).

In some embodiments it may be necessary to adapt the control loop in order to compensate for fluid removed from one of the containers 68, 78, 48 in the manner described, because such fluid flow control loop, controlling the flow rate or rates for respective pumps 62, 72, 42, may be based on the weight or change of weight of a respectively associated container 68, 78, 48.

FIGS. 3, 3A, 3B, 3C, and 3D schematically show an extracorporeal blood treatment apparatus in accordance with a second embodiment of the present invention. The blood circuit BC is only represented schematically because may be the same as disclosed in the example of prior art of FIG. 1.

The hydraulic circuit in accordance with the second embodiment of the present invention also includes an air detector array 200 as described above with respect to the first embodiment. Further, the hydraulic circuit in accordance with the second embodiment of the present invention also includes a fresh fluid dispatcher 300 and an air and fluid drainer 400 as described above with respect to the first embodiment, with the exception of what is described below.

The fluid dispatcher 300 in accordance with the second embodiment includes four two-way valves 326, 327, 324 and 326'. Valve 326' (flow controller) is arranged on the pre blood pump (PBP) line 60, which is routed through the fluid dispatcher 300 downstream from pre blood (PBP) pump 62.

Pre blood pump line 60 branches off (pre blood pump line branch 600) to valve 326, which connects pre blood pump line 60 to the common zone 310. Valves 327 and 324 respectively connect infusion line 70 and dialysate/infusion line 40 to common zone 310 through pre-infusion line branch 700 and a dialysate line branch 800.

The air and fluid drainer 400 in accordance with the second embodiment also includes a flow controller 452 (e.g. a two-way valve), connecting the common zone 310 to the drainer fluid line 450 and further to the effluent line 50, upstream of blood leak detector (BLD) 53. In the second embodiment, the flow controller 452 comprises a two-way valve. Including a pump in flow controller 452 is not necessary since a pumping action may be provided by a respective one (or more) of pumps 62, 72, 42. A non-return flow controller 456 is provided in drainer fluid line 450. The non-return flow controller 456 (e.g. a check valve) is configured to allow fluid flow from the drainer fluid line 450 towards and into the effluent line 50, while preventing fluid flow in the opposite direction.

The second embodiment also addresses problems FB1, FB2, and EB1, as described above with respect to the first embodiment. Further, the second embodiment addresses problems FB3 and FB4 (see above). The fluid dispatcher 300 may be configured to allow fluid from any one container 68, 78, 48 to be directed to any infusion site (e.g. through any of lines 60, 70, 70*b*, 40) by controlling valves 326, 327, 324, and 326'. Likewise, the fluid dispatcher 300 may be configured to allow a customized fluid to be directed to any infusion site, the customized fluid being created by mixing of fluids from any two containers 68, 78, 48.

Figures 3, 3A:
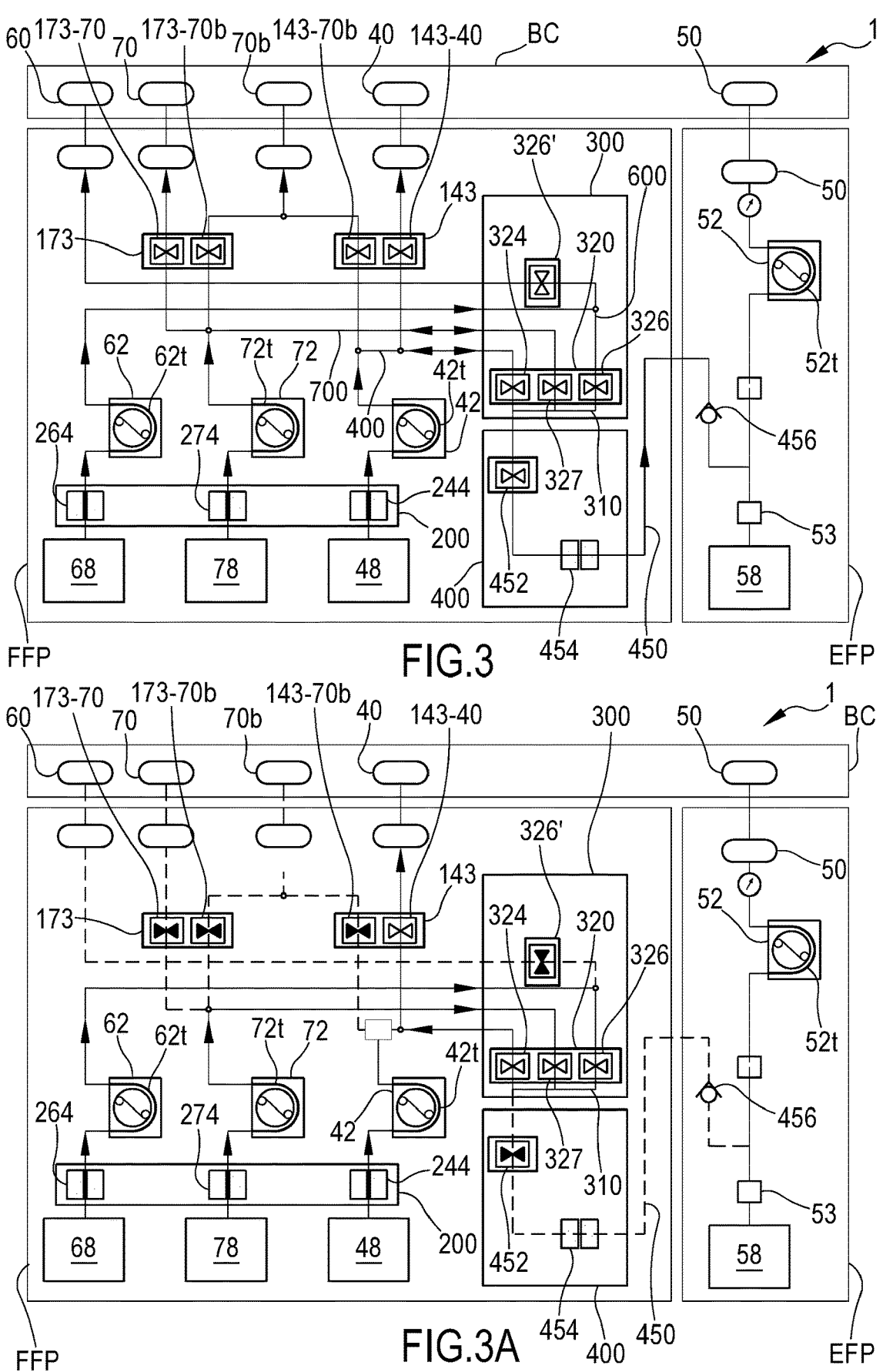
FIGS. 3, 3A, 3B, 3C schematically show an extracorporeal blood treatment apparatus in accordance with a second embodiment of the present invention.

FIGS. 3A and 8 schematically shows an example configuration of the extracorporeal blood treatment apparatus in accordance with the second embodiment of the present invention. As described above, the fresh fluid dispatcher 300 may be configured to alternatively associate one or more connected containers 68, 78, 48 to a single injection site (here: supplying dialysate to the treatment unit 10). The example of FIG. 3A shows a configuration in which fluid from all containers 68, 78, 48 is supplied to the dialysate line 40. Similar to a corresponding configuration based on the first embodiment (see FIG. 2A and corresponding description above) valves 326, 327, and 324 are open while valve 326' is closed. In contrast, pumps 62, 72, and 42 are all controlled to supply (the same) fluid to the dialysate line 40, valve arrays 143 and 173 being controlled accordingly (see FIG. 3A; valves 173-70, 173-70*b*, and 143-70*b* being closed, valve 143-40 being open). In detail, pumps 62 and 72 are controlled to supply fluid from containers 68 and 78, via fluid dispatcher 300, to dialysate line 40, while pump 42 is controlled to supply fluid from container 48 directly to dialysate line 40. This addresses the above-described problem FB2 and further allows replacement of an empty container without stopping blood circulation and/or therapy. Any container 68, 78, 48 may be replaced during an ongoing treatment since fluid from the remaining container or containers may be supplied as shown. As each fluid pump 62, 72, 42 is controlled to deliver fluid from each associated container 68, 78, 48 only, this configuration does not have any impact on a fluid balancing system control loop since the flow-rate of each pump is associated to the weighting of the respective single associated container.

Figure 3B:
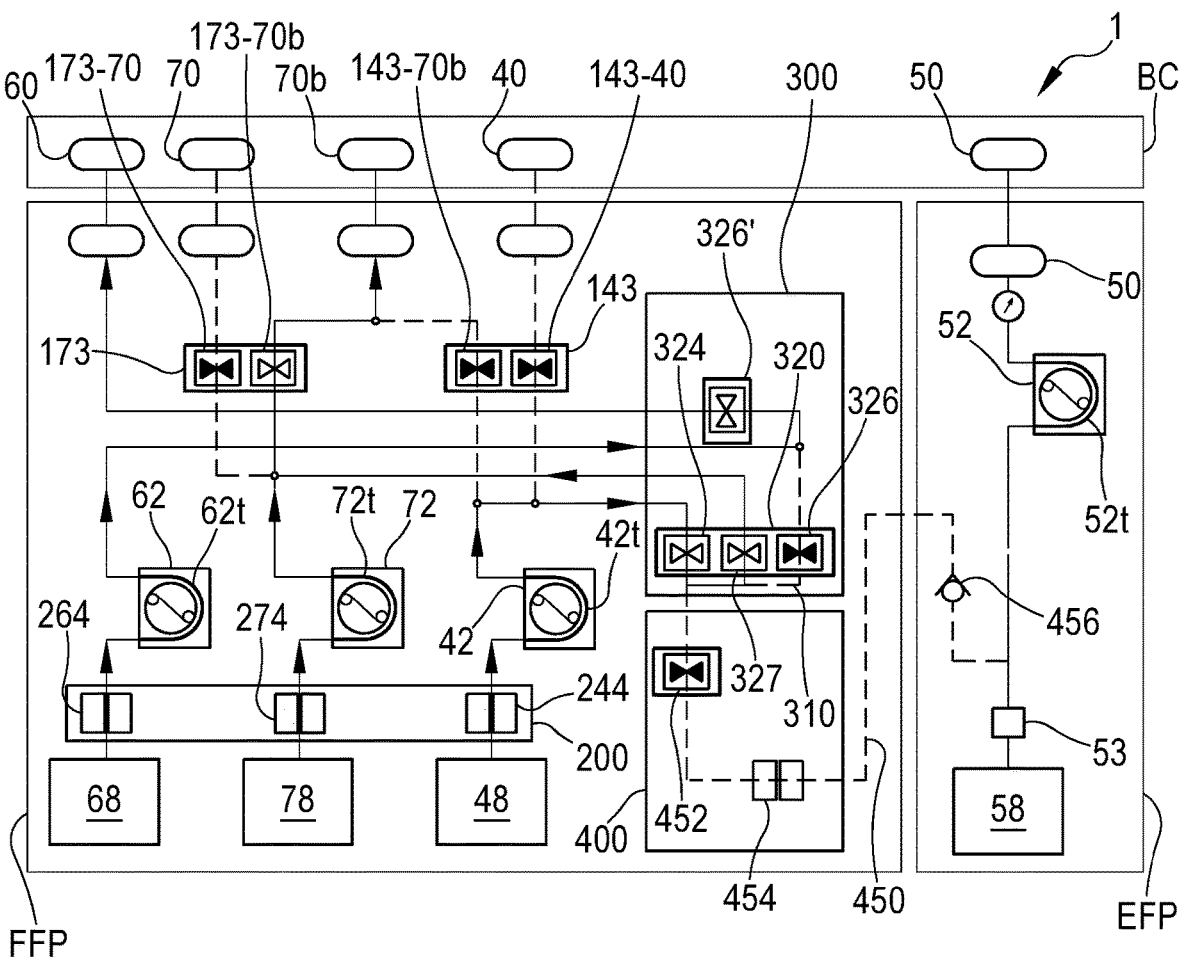
Figure 3C:
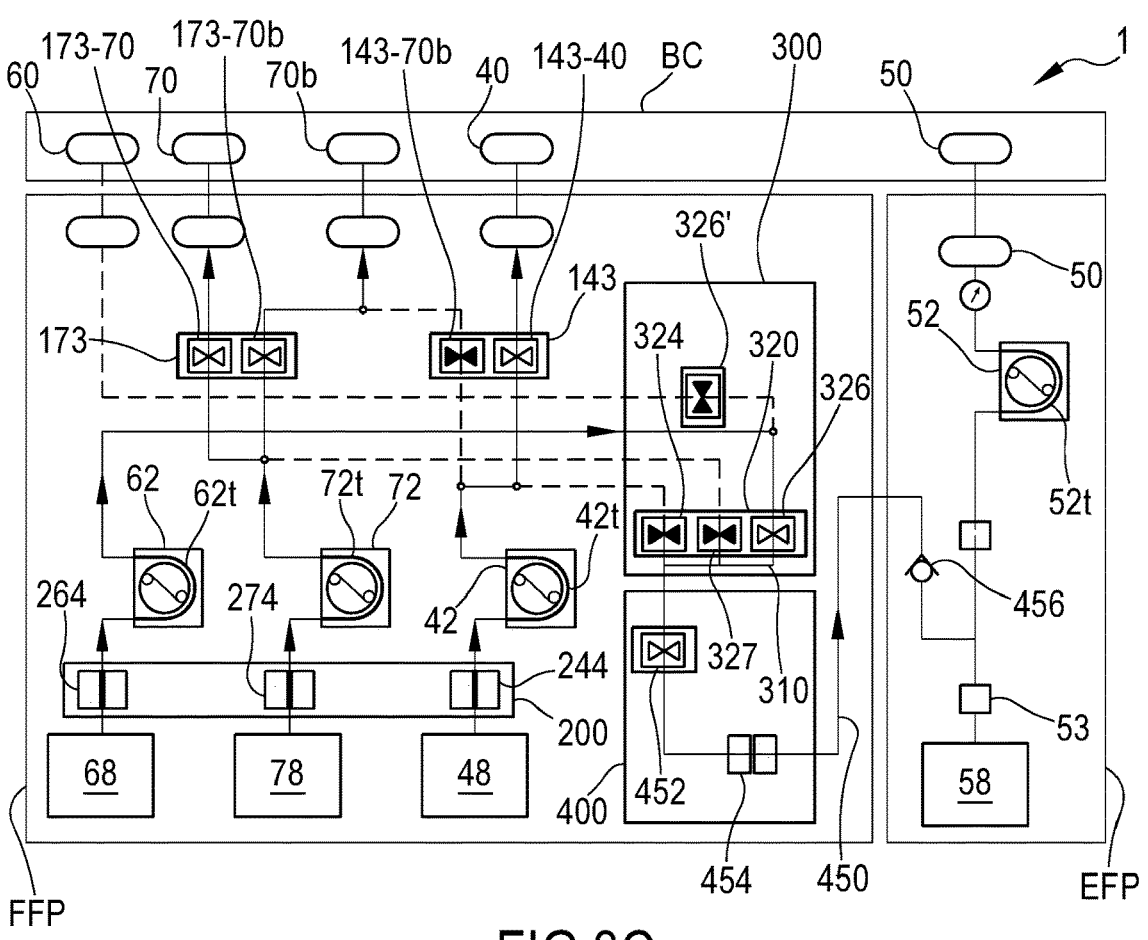

FIGS. 3B and 10 schematically shows another example configuration of the extracorporeal blood treatment apparatus in accordance with the second embodiment of the present invention. As described above, the fresh fluid dispatcher 300 may be configured to allow mixing of fluids coming from two separate containers 68, 78, 48 at a defined ratio and to infuse the mixture to a single site (or several sites) on the blood or dialysate side (e.g. lines 70, 70*b* and/or 40). The example of FIG. 3C shows a configuration in which fluids from the replacement fluid and dialysate containers 78, 48 are mixed at a defined ratio and supplied to the post-infusion line 70*b* while fluid from the pre blood pump (PBP) container 68 is supplied, by the pre blood pump 62 and via fluid dispatcher 300, to pre blood pump (PBP) line 60. Valves 173-70*b*, 324, 327 and 326' are controlled to open, while valves 173-70, 143-70*b*, 143-40 and 326 are controlled to close. Replacement fluid pump 72 and dialysate pump 42 are controlled to operate, each at a pre-determined rate in order to achieve the desired mixing ratio, thereby respectively supplying fluid from the containers 78 and 48, via the fluid dispatcher 300, to the post infusion line 70*b*. The pre blood ump 62 is controlled to supply fluid from the pre blood pump container 68 to the pre blood pump (PBP) line 60, also via the fluid dispatcher 300. Mixing of pre blood pump (PBP) fluid with the other fluids going through the fluid dispatcher 300 is prevented due to the first valve 326 being kept closed.

FIGS. 3C and 9 schematically show another example configuration of the extracorporeal blood treatment apparatus in accordance with the second embodiment of the present invention. When air is detected (see problem FB1 above) upstream from a fluid pump (in the example shown, upstream the pre blood (PBP) pump 62), the pump is stopped in order to avoid introduction of air into the blood circuit BC. If the associated fluid container, here the pre blood pump container 68, is empty, an operator may change the container. After that, the relevant valve (here the first valve 326) may be opened in the fluid dispatcher 300 and the flow controller 452 in the air and fluid drainer 400 may be controlled to open (other valves 327, 324, 326' remain closed or are controlled to close). Subsequently, the respective pump (in this example, the pre blood pump 62) is controlled to remove air from the affected circuit segment (in the example shown between the pre blood pump container 68 and the common zone 310 of the fluid dispatcher 300) and sends it to the effluent line 50 via the drainer fluid line 450. The respective pump (here, pre blood pump 62) may be controlled to operate while air is detected by the respective upstream air detector (here air detector 264). When there is no more air detected at the upstream air detector, the respective pump (here, pre blood pump 62) is further controlled to operate in order to fill the entire circuit of the fluid dispatcher 300 and the drainer 400 up to the downstream drainer air detector 454 with liquid in order to ensure that the common zone 310 of the fluid dispatcher 300 is free from air. It is noted that, during this procedure, it may be necessary to deactivate/disable the blood leak detector (BLD) 53 in order to prevent a false alarm (e.g. due to the detection of air by the blood leak detector 53). As shown in FIG. 3D, the replacement fluid pump 72 and the dialysate pump 42 may be controlled to continue to operate and, thus, continue to supply, respectively, infusion fluid from the replacement fluid container 78 and dialysate or infusion fluid from dialysate/infusion container 48 to lines 70/70*b* and 40. Valve arrays 173 and 143 may be set as desired, while valves 327 and 324 of the fluid dispatcher 300 are controlled to remain closed. The configuration shown in FIG. 3C addresses problem FB1 as described above.

The hydraulic circuits and structures in accordance with embodiments of the present invention facilitate great modularity in the management of fluids, air in fluid removal, and rinsing of the BLD. Further, the possibility to distribute any of the supplied fluids to a single location or site of the hydraulic circuit flow-path facilitates a potential integration of a fluid analysis sensor at such a location or site. Owing to its position on effluent circuit, such devices may be used to carry out measurements on effluent fluid but also on fresh fluid from containers 68, 78, 48. Several sensing technologies (spectrometry, electrochemistry, optode) may be employed in analyzing electrolytes and solutes of clinical interest of the fluids. Such circuit structure allows comparison of two consecutive measurements made by a same sensor onto two fluids samples.

For fresh fluids, it is possible to check before use if the composition of a new connected fluid container is the same as previous one (e.g. for verifying whether a multi-compartment bag has been well mixed, or whether a citrated PBP container is set up as replacement container). Such circuit structure allows comparing change in effluent composition versus fresh dialysate, fresh dialysate being used as reference sample. Such circuit structure allows detecting presence and also citrate concentration in PBP container.

Comparative measurement allows simplification and improvement of the accuracy of adsorption spectrometric and electrochemistry methods. The possibility to periodically rinse with fresh solutions amperometric/potentiometric electrochemistry sensors allows limitation of bias or polarization over time.

Figure 4:
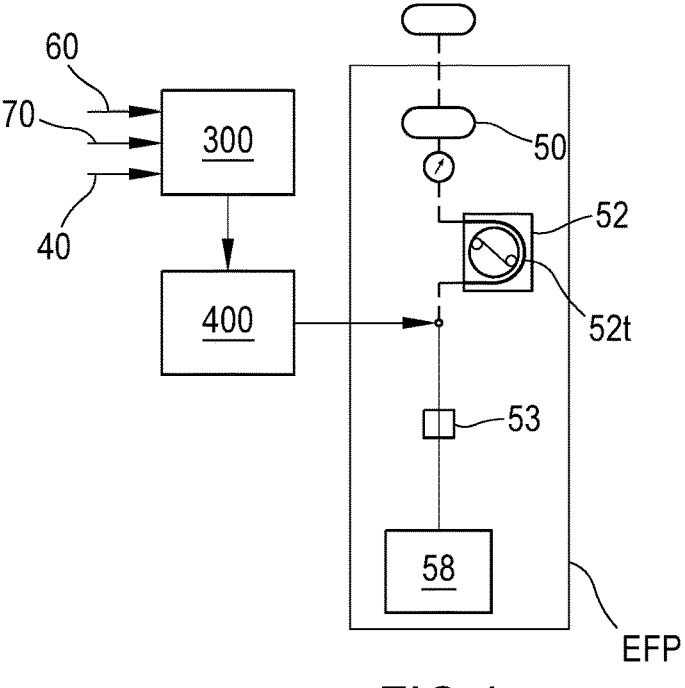
FIG. 4 schematically shows rinsing and calibration of a BLD sensor in accordance with embodiments of the present invention.

FIG. 4 schematically shows rinsing and calibration of the blood leak detector BLD 53 in accordance with embodiments of the present invention. As shown, in order to address above-described problem EB1, fresh fluid (e.g. pre blood pump PBP fluid, replacement fluid, or dialysate fluid) from any one or more of containers 68, 78, 48 (not shown) may be supplied to the fresh fluid dispatcher 300 and further, via the air and fluid drainer 400 to the effluent line 50. While fresh fluid is delivered and with the effluent pump 52 being controlled to stop, the blood leak detector BLD 53 may be (re-) calibrated. In detail, the blood leak detector BLD 53 may be filled, in the manner described, with fresh dialysate or replacement fluid, such that the (re-) calibration may be performed and/or controlled by the control unit 80 (not shown). Since the fresh fluid from any one of the containers 68, 78, 48 used for recalibrating the blood leak detector BLD 53 may be collected by the effluent container 58, the general principle for monitoring patient weight loss, which manages the activity of the effluent pump 52 isn't affected by this process. As for air in fresh fluids removal, the patient weight loss may always be calculated as the whole effluent weight minus the weight of all already used fresh fluids.

Figure 5:
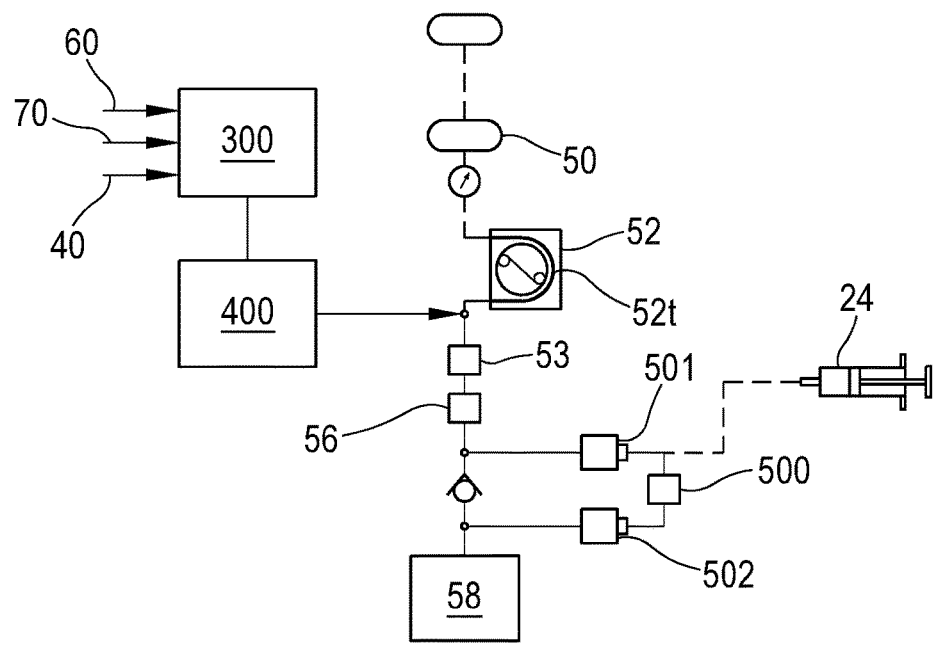
FIG. 5 schematically shows integration of a fluid analyzer and/or fluid sampler in accordance with embodiments of the present invention.

FIG. 5 schematically shows integration of a fluid analyzer and/or fluid sampler in accordance with embodiments of the present invention (in order to address above-described problem FB5). An integrated on line fluid analyzer 56 may be arranged on the effluent line 50 in order to determine properties of fluid going through line 50 or an external fluid analyzer 500 may be connected to the effluent line 50 via interface ports 501 and 502. Further, a non-return valve 57 (e.g. a check valve, see FIG. 6) may be arranged on the effluent line 50 in order to prevent back flow of unknown fluid from the effluent container 58 and/or a drain (not shown).

The use of the optional external fluid analyzer 500 may be required if the sensor technology isn't compatible with the CRRT set sterilization process. Otherwise some sensors may require wait states in their measurement process without flowing of a fluid sample. In such cases the external fluid analyzer 500 may be required to manage its own sampling pump (e.g. exhibiting a sampling flow rate lower than the fluid flow rate towards the effluent container 58; see FIG. 6 and the corresponding description below). The zone of the effluent circuit including the non-return valve 57 allows to maintain fluid flow. A syringe pump 24 may be connected to a line connecting the external fluid analyzer 500 to the interface ports 501 and 502.

Figure 6:
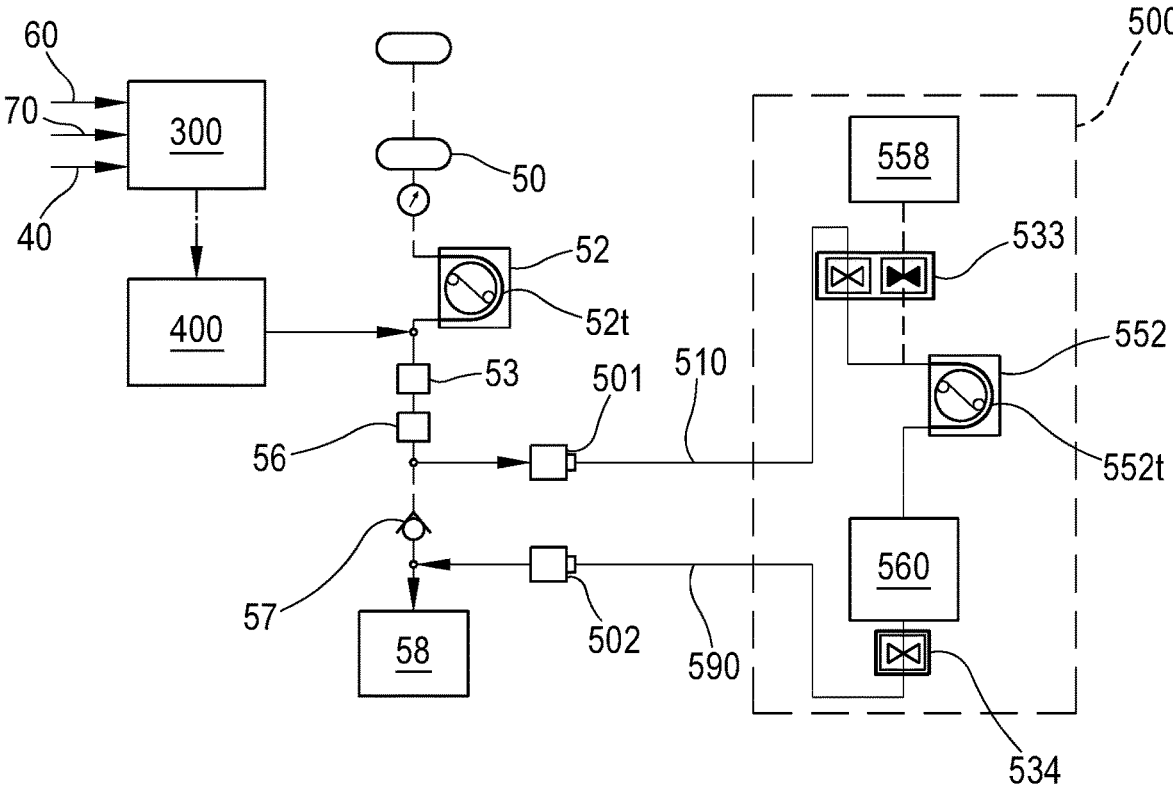
FIG. 6 schematically shows integration of an external fluid analyzer in accordance with embodiments of the present invention.

FIG. 6 schematically shows integration of the external fluid analyzer 500 in accordance with embodiments of the present invention. In line with the general configuration is shown in FIG. 5, FIG. 6 shows further details with respect to the external fluid analyzer 500. The external fluid analyzer 500 includes, if required, an analyzer rinsing and calibration solution container 558, a valve array 533 configured to selectively allow fluid flow from the calibration container 558 and/or from an inlet line 510 towards a sampling pump 552 and towards an array 560 of sensors configured to determine properties of the fluid going through the external fluid analyzer 500. Further, a valve 534 is configured to selectively allow fluid to flow from the array 560 through an outlet line 590 and back towards the effluent line 50 and into the effluent container 58 or the drain (not shown). The outlet line 590 of the fluid analyzer 500 being in fluid connection with the effluent container 58 facilitates using said effluent container 58 also for collecting waste fluid from the fluid analyzer 500. If the fluid analyzer 500 should require significant amounts of calibration or rinsing solution from the calibration container 558, such additional fluid volumes may be taken into account in the CRRT monitor fluid balance.

FIG. 7 shows a third embodiment of the present invention similar to the second embodiment. In this third embodiment, the replacement fluid from the respective container 78 may be routed pre or post treatment unit 10. A post-filter infusion line 70c is connected between the treatment unit 10 and the blood warmer 33. The dialysate circuit has no capability for being routed to post-infusion 70b as it was the case in first and second embodiment. An additional fluid circuit (additional fluid container 88, additional pump 82, fourth valve 328, air detector 284, additional post-infusion line 70d with a flow controller valve 328') is added to deliver post-infusion directly to the air separator/bubble trap 35. Further flow controller valves 324', 326' are placed on the dialysate line 40 and on the pre blood pump (PBP) line 60.

The blood circuit BC, the dialysate line 40, the pre blood pump (PBP) line 60, the pre-infusion line 70, the post-infusion lines 70b, 70c, 70d, the effluent line 50 may be part of a disposable assembly according to an independent aspect of the invention.

Said lines are made of flexible plastic tubes and have respective sections configured to be coupled the respective fluid pumps or air detectors or flow controllers. The fluid lines may be connected one to the other, at the common zone, through bonding, welding or joints, optionally Y or T joints.

The apparatus as disclosed above comprises a machine comprising a main body with the pumps, the control unit, sensors and controllers and possible other elements configured to hold the various parts of the disposable assembly. The disposable assembly is coupled to the machine for performing one treatment on one patient only and disposed after use.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:

1. An apparatus for extracorporeal blood treatment, comprising:

a treatment unit;

a blood circuit coupled to the treatment unit and comprising a blood removal line and a blood return line configured to connect to a vascular system of a patient;

a blood pump configured to couple to a pump section of the blood circuit;

a plurality of fluid lines having first ends configured to connect to respective containers and having second ends located at infusion sites on the blood removal line and/or on the blood return line and having second ends connected to the treatment unit;

a plurality of pumps active on the plurality of fluid lines and configured to pump fluid of the containers to the infusion sites on blood removal line and/or on the blood return line and to or from the treatment unit; and a fluid dispatcher comprising a common zone, wherein at least two fluid lines of said plurality of fluid lines are connected one to the other at said common zone upstream of the infusion sites on the blood removal line and on the blood return line and of the treatment unit to selectively allow fluid flow between said at least two fluid lines through said common zone.

2. The apparatus of claim 1, wherein said plurality of fluid lines comprises a plurality of infusion lines comprising at least one of the second ends located at an infusion site on the blood removal line or on the blood return line; wherein some pumps of the plurality of pumps are active on said plurality of infusion lines; wherein at least two infusion lines of said plurality of infusion lines are connected one to the other at said common zone.

3. The apparatus of claim 1, wherein said plurality of fluid lines comprises:

a dialysate circuit comprising a dialysate line comprising a respective first end configured to connect to a dialysate container and a respective second end connected to the treatment unit; and an effluent line configured to discharge fluid from the treatment unit;

wherein the plurality of pumps comprises a dialysate pump active on the dialysate line and an effluent pump active on the effluent line;

wherein the dialysate line and the effluent line are connected one to the other at said common zone.

4. The apparatus of claim 3, comprising a drainer, wherein the drainer comprises a drainer fluid line configured to connect the common zone of the fluid dispatcher to the effluent line, and a drainer flow controller configured to selectively allow fluid flow between the common zone and the effluent line.

5. The apparatus of claim 4, wherein the drainer flow controller comprises an occlusive pump.

6. The apparatus of claim 4, comprising a plurality of flow controllers placed on the plurality of fluid lines and between the pumps and the infusion sites on one or more of: the blood removal line, the blood return line, and the treatment unit, wherein each flow controller comprises a two-way valve configured to selectively allow or prevent fluid flow;

and wherein the drainer flow controller comprises a two-way valve configured to selectively allow or prevent fluid flow.

7. The apparatus of claim 4, wherein the drainer comprises a drainer air detector arranged on the drainer fluid line and configured to detect gas in a liquid fluid flow between the common zone of the fluid dispatcher and the effluent line.

8. The apparatus of claim 4, comprising a control unit connected to the pumps and to the fluid dispatcher, the apparatus also comprising an air detector array placed upstream or downstream the pumps and configured to detect gas in at least one of the fluid lines of the plurality of fluid lines; wherein the control unit is connected to the drainer and to the air detector array; wherein the control unit is configured to command execution of a task for removing air, said task comprising:

receiving a signal from the air detector array indicative of detected gas upstream at least one of the pumps;

stopping said at least one of the pumps where gas is detected; and activating the drainer and controlling the fluid dispatcher to remove the gas.

9. The apparatus of claim 1, wherein said plurality of fluid lines comprises:

a pre blood pump line comprising a respective first end configured to connect to a pre blood pump container and a respective second end located at an infusion site on the blood removal line;

a pre-infusion line comprising a respective first end configured to connect to an infusion container and a respective second end located at an infusion site on the blood removal line downstream from the blood pump and at least one post-infusion line comprising a respective first end configured to connect to an infusion container and a respective second end located at an infusion site on the blood return line; and a dialysate circuit comprising a dialysate line comprising a respective first end configured to connect to a dialysate container and a respective second end connected to the treatment unit;

wherein an effluent line is configured to discharge fluid from the treatment unit;

wherein the plurality of pumps comprises a pre blood pump active on the pre blood pump line and an infusion pump active on the pre-infusion line and a dialysate pump active on the dialysate line and wherein an effluent pump is active on the effluent line.

10. The apparatus of claim 1, wherein the fluid dispatcher comprises a plurality of valves placed at the common zone and configured to selectively allow fluid flow between said at least two fluid lines.

11. The apparatus of claim 1, wherein the fluid dispatcher is configured to allow a bidirectional flow in at least part of said at least two fluid lines.

12. The apparatus of claim 1, wherein the fluid dispatcher comprises a valve on each of said at least two fluid lines of the plurality of fluid lines to selectively allow fluid flow between the respective fluid line and the common zone.

13. The apparatus of claim 12, wherein each of said at least two fluid lines of the plurality of fluid lines comprises, upstream from the respective pump with respect to a fluid flow from the respective container, a branch connected to the respective valve.

14. The apparatus of claim 1, comprising a plurality of flow controllers placed on the plurality of fluid lines and between the plurality of pumps and the infusion sites on one or more of: the blood removal line, the blood return line, and the treatment unit.

15. The apparatus of claim 14, wherein at least one of the plurality of flow controllers is placed on two or more fluid lines of the plurality of fluid lines and is configured to selectively allow fluid flow into one or more of said two or more fluid lines of the plurality of fluid lines.

16. The apparatus of claim 1, further comprising an air detector array configured to detect gas on each of said at least two fluid lines, wherein the air detector array comprises an air detector arranged on each of said at least two fluid lines of the plurality of fluid lines, each air detector being arranged on the respective line proximate the respective container and/or immediately downstream from the respective pump with respect to a fluid flow from the container.

17. The apparatus of claim 16, wherein each of said at least two fluid lines of the plurality of fluid lines includes, upstream or downstream the respective pump with respect to a fluid flow from the respective container, a branch, wherein said branches are connected one to the other at the common zone.

18. The apparatus of claim 1, comprising a control unit connected to the pumps and to the fluid dispatcher; wherein the control unit is configured to:

control at least one of said pumps and to control the fluid dispatcher so that fluid from one or more of the containers is conveyed to the second end of one or more of the fluid lines of the plurality of fluid lines; or control at least two of said pumps and to control the fluid dispatcher so that fluids from said at least two pumps is mixed and then conveyed to the second end of one or more of the fluid lines of the plurality of fluid lines.

19. An apparatus for extracorporeal blood treatment, comprising:

a treatment unit;

a blood circuit coupled to the treatment unit and comprising a blood removal line and a blood return line configured to connect to a vascular system of a patient;

a blood pump configured to couple to a pump section of the blood circuit;

a dialysate circuit comprising a dialysate line comprising a first end configured to connect to a dialysate container and a second end connected to the treatment unit;

an effluent line configured to discharge fluid from the treatment unit;

a plurality of infusion lines comprising first ends configured to connect to infusion containers and second ends located at infusion sites on the blood removal line and/or on the blood return line;

a dialysate pump active on the dialysate line;

an effluent pump active on the effluent line;

a plurality of pumps active on said plurality of infusion lines and configured to pump fluid of the containers to the infusion sites on blood removal line and/or on the blood return line;

a fluid dispatcher comprising a common zone, wherein the dialysate line and the effluent line are connected one to the other at said common zone to selectively allow fluid flow between the dialysate line and the effluent line through said common zone;

wherein at least two fluid lines of said plurality of infusion lines are connected one to the other at said common zone upstream the infusion sites on blood removal line and on the blood return line to selectively allow fluid flow between said at least two fluid lines through said common zone.

20. An apparatus for extracorporeal blood treatment, comprising:

a treatment unit;

a blood circuit coupled to the treatment unit and comprising a blood removal line and a blood return line configured to connect to a vascular system of a patient;

a blood pump configured to couple to a pump section of the blood circuit;

a dialysate circuit comprising a dialysate line comprising a first end configured to connect to a dialysate container and a second end connected to the treatment unit;

an effluent line configured to discharge fluid from the treatment unit;

a plurality of infusion lines comprising first ends configured to connect to infusion containers and second ends located at infusion sites on the blood removal line and/or on the blood return line;

a dialysate pump active on the dialysate line;

an effluent pump active on the effluent line;

a plurality of pumps active on said plurality of infusion lines and configured to pump fluid of the containers to the infusion sites on blood removal line and/or on the blood return line;

a fluid dispatcher comprising a common zone;

wherein at least two fluid lines of said plurality of infusion lines are connected one to the other at said common zone upstream the infusion sites on blood removal line and on the blood return line to selectively allow fluid flow between said at least two fluid lines through said common zone.

* * * * *